United States Patent [19]

Lorch et al.

[11] Patent Number: 5,328,841

[45] Date of Patent: Jul. 12, 1994

[54] METHODS FOR ISOLATING EG III CELLULASE COMPONENT AND EG III CELLULASE IN POLYETHYLENE GLYCOL USING INORGANIC SALT AND POLYETHYLENE GLYCOL

[75] Inventors: Jeffrey D. Lorch, Hudson, Wis.; Kathleen A. Clarkson, San Francisco, Calif.; Edmund Larenas, San Carlos, Calif.; Benjamin S. Bower, San Francisco, Calif.; Geoffrey L. Weiss, San Francisco, Calif.

[73] Assignee: Genencor International, Inc., South San Francisco, Calif.

[21] Appl. No.: 862,846

[22] Filed: Apr. 3, 1992

Related U.S. Application Data

[63] Continuation-in-part of Ser. No. 707,647, May 30, 1991, which is a continuation-in-part of Ser. No. 668,640, Mar. 13, 1991, which is a continuation-in-part of Ser. No. 593,919, Oct. 5, 1990, abandoned, and a continuation-in-part of Ser. No. 770,049, filed as PCT/US91/07276, Oct. 4, 1991.

[51] Int. Cl.$^5$ .................... C12N 9/42; C12N 1/18; C12N 1/00
[52] U.S. Cl. .................... 435/209; 435/256.7; 435/945
[58] Field of Search ................ 435/209, 945, 256.7

[56] References Cited

U.S. PATENT DOCUMENTS

| | | | |
|---|---|---|---|
| 3,415,804 | 12/1968 | Polson | 260/112 |
| 4,016,039 | 4/1977 | Schreiber | 195/66 R |
| 4,144,130 | 3/1979 | Kula et al. | 195/66 R |
| 4,275,163 | 6/1981 | Gallo | 435/209 |
| 4,343,735 | 8/1982 | Menge et al. | 260/112 R |
| 4,435,307 | 3/1984 | Barbesgaard et al. | 252/174.12 |
| 4,439,358 | 3/1984 | Coan et al. | 260/112 B |
| 4,470,969 | 9/1984 | Pancham et al. | 424/101 |
| 4,472,504 | 9/1984 | Gallo | 435/209 |
| 4,479,881 | 10/1984 | Tai | 252/8.8 |
| 4,487,831 | 12/1984 | Day et al. | 435/99 |
| 4,508,825 | 4/1985 | Kim et al. | 435/201 |
| 4,591,563 | 5/1986 | Paul et al. | 435/193 |
| 4,648,979 | 3/1987 | Parslow et al. | 252/8.8 |

(List continued on next page.)

FOREIGN PATENT DOCUMENTS

| | | |
|---|---|---|
| 0120528 | 10/1984 | European Pat. Off. |
| 0137280 | 4/1985 | European Pat. Off. |
| 0173397 | 3/1986 | European Pat. Off. |
| 0220016 | 4/1987 | European Pat. Off. |
| 0244234 | 11/1987 | European Pat. Off. |
| 0271004 | 6/1988 | European Pat. Off. |
| 2148278 | 3/1972 | Fed. Rep. of Germany |
| 58-36217 | 3/1983 | Japan |
| 58-54082 | 3/1983 | Japan |
| 64-40681 | 2/1989 | Japan |
| 85/04672 | 10/1985 | PCT Int'l Appl. |
| 89/09259 | 10/1989 | PCT Int'l Appl. |
| 91/05841 | 5/1991 | PCT Int'l Appl. |
| 1368599 | 10/1974 | United Kingdom |
| 2094826 | 9/1982 | United Kingdom |
| 2095275 | 9/1982 | United Kingdom |

OTHER PUBLICATIONS

S. Aho, "Structural and functional analysis of *Trichoderma reesei* endoglucanase 1 expressed in yeast *Saccharomyces cerevisiae*", FEBS Letters, vol. 291, pp. 45–49 (1991).

Andersson et al., "α-Amylase production in aqueous two-phase systems with *Bacillus subtilis*", Enzyme and Microb. Technol., vol. 7, pp. 333–338, (1985).

Berg et al., "Enzyme-Gold Affinity Labelling of Cellu- (List continued on next page.)

Primary Examiner—David M. Naff
Assistant Examiner—Michael V. Meller
Attorney, Agent, or Firm—Karen I. Krupen

[57] ABSTRACT

Methods for isolating EG III cellulase component and enriched EG III cellulase in polyethylene glycol are disclosed. The methods comprise adding an inorganic salt and polyethylene glycol having a molecular weight of from about 5,000 to 10,000 to an aqueous mixture of cellulase proteins under conditions to create a two-phase system. Next, the cellulase proteins other than EG III are separated in an EG III-poor aqueous phase while EG III cellulase component is retained in an EG III-rich polyethylene glycol phase. Lastly, the EG III component can be separated from the polyethylene glycol. The preferred method of separation is alcohol precipitation.

9 Claims, 9 Drawing Sheets

U.S. PATENT DOCUMENTS

| | | | |
|---|---|---|---|
| 4,661,289 | 4/1987 | Parslow et al. | 252/547 |
| 4,683,294 | 7/1987 | Van Wijendaele et al. | 530/371 |
| 4,684,723 | 8/1987 | Dove et al. | 530/351 |
| 4,697,003 | 9/1987 | Coan | 530/380 |
| 4,725,544 | 2/1988 | Tan et al. | 435/200 |
| 4,728,613 | 3/1988 | Brewer et al. | 435/222 |
| 4,738,682 | 4/1988 | Boegh et al. | 8/401 |
| 4,762,788 | 8/1988 | Warzywoda et al. | 435/209 |
| 4,797,361 | 1/1989 | Montenecourt | 435/198 |
| 4,822,516 | 4/1989 | Suzuki et al. | 252/174.12 |
| 4,832,864 | 5/1989 | Olson | 252/174.12 |
| 4,894,338 | 1/1990 | Knowles et al. | 435/172.3 |
| 4,912,056 | 3/1990 | Olson | 435/263 |
| 4,945,053 | 7/1990 | Ito et al. | 435/209 |
| 4,952,505 | 8/1990 | Cho | 435/209 |
| 4,978,470 | 12/1990 | Suzuki et al. | 252/174.12 |
| 5,006,126 | 4/1991 | Olson et al. | 8/401 |
| 5,045,464 | 9/1991 | Ito et al. | 435/209 |
| 5,120,463 | 6/1992 | Bjork et al. | 252/174.12 |
| 5,139,943 | 8/1992 | Heinsohn et al. | 435/226 |
| 5,151,358 | 9/1992 | Heinsohn et al. | 435/226 |

(List continued a next page.)

OTHER PUBLICATIONS lose", *Journal of Electron Microsc. Tech.*, vol. 8, pp. 371–379, (1988) [Abstract].

Bhat et al., *Carbohydrate Research*, vol. 190, pp. 279–297 (1989).

Brown et al., "Microbial Enzymes and Lignocellulose Utilization," *Genetic Control of Environmental Pollutants*, Omen Editor, Plenum Publishing Corp., pp. 239–265 (1984).

Chen et al., "Nucleotide Sequence and Deduced Primary Structure of Cellobiohydrolase II from *Trichoderma reesei*", *Biotechnology*, vol. 5, pp. 274–278 (1987).

Corrick et al., *Gene* vol. 53, pp. 63–71 (1987).

Coughlan et al., "Comparative Biochemistry of Fungal and Bacterial Cellulolytic Enzyme Systems", *Biochemistry and Genetics of Cellulose Degradation*, Aubert et al., Editors, pp. 11–30 (1988).

Hakanssan, Dissertation, Faculty of Science, Uppsala University, pp. 6–23 (1981).

Hakansson et al., *Biochimica et Biophysica Acta* vol. 524, pp. 385–392 (1978).

Harkki et al., "Genetic engineering of *Trichoderma* to produce strains with novel cellulase profiles", *Enzyme Microb. Technol.*, vol. 13, pp. 227–233 (1991).

Hayashida et al., "Cellulases of *Humicola insolens* and *Humicola grisea*", *Methods in Enzymology*, vol. 160, pp. 323–332 (1988).

Hayashida et al., "Production and Purification of Thermostable Cellulases from *Humicola insolens* YH-8", *Agri. Biol. Chem.*, vol. 44(8), pp. 1721–1728 (1980).

Hayashida et al., "The Role of Carbohydrate Moiety on Thermostability of Cellulases from *Humicola insolens* YH-8", *Agri. Biol. Chem.*, vol. 44(3) pp. 481–487 (1980).

*International Textile Bulletin, Dyeing/Printing/Finishing*, 2nd Quarter, pp. 5–8 (1990);

JTN, "Weight Loss Treatment to Soften the Touch of Cotton Fabric", p. 64 (Dec. 1988).

Kenkyushitsu et al., "The Improvement of Cellulose Fibers by Means of Cellulase".

Knowles et al., "The Use of Gene Technology in the Development of Novel Cellulolytic Organisms—*Trichoderma reesei* Cellulase and Cellulobiohydrolase Gene Cloning and Expression; a Review", *Recent Adv. Biotechnol. Appl. Biol.*, pp. 139–142 (1988) [Abstract].

Knowles et al., "The use of gene technology to investigate fungal cellulolytic enzymes *Trichoderma reesei* cellulase complex gene cloning and expression in *Saccharomyces cerevisiae*", *FEMS Symp. 43*, pp. 153–169 (1988) [Abstract].

Kubicek-Pranz et al., "Transformation of *Trichoderma reesei* with cellobiohydrolase II gene as a means for obtaining strains with increased cellulase production and specific activity", *Journal of Biotechnology*, vol. 20, pp. 83–94 (1991).

Kubicek-Pranz et al., "Characterization of Commercial *Trichoderma-reesei* Cellulase Preparations by Denaturing Electrophoresis SDS-PAGE and Immunostaining Using Monoclonal Antibodies", *Biotechnol. Appl. Biochem.*, vol. 14, pp. 317–323 (1991) [Abstract].

Kula et al., "Purification α-Enzymes by Liquid–Liquid Extraction", pp. 73–118, Adv. Biochem. Eng., 24, 1982.

Luderer et al., "A Re-appraisal of Multiplicity of Endoglucanase I from *Trichoderma reesei* Using Monoclonal Antibodies and Plasma Desorption Mass Spectrometry", *Biochim. Biophys. Acta*, vol. 1076, pp. 427–434 (1991) [Abstract].

Miller et al., "Direct and Indirect Gene Replacements in *Aspergillus nidulans,*" *Mol. and Cell. Biol.*, vol. 5(7), pp. 1714–1721 (1985).

Murphy-Holland et al., "Secretion activity and stability of deglycosylated cellulase of *Trichoderma reesei* gene (List continued on next page.)

OTHER PUBLICATIONS cloning", *Abstr. Annu. Meet. Am. Soc. Microbiol.*, 85 Meet., 193 (1985) [Abstract].

Ohishi et al., "Reformation of Cotton Fabric by Cellulase," pp. 1–12.

Penttilla et al., "Homology between cellulase genes of *Trichoderma reesei*: complete nucleotide sequence of the endoglucanase I gene", *Gene*, vol. 45, pp. 253–263 (1986).

Penttillä et al., "Expression of Two *Trichoderma reesei* Endoglucanases in the Yeast *Saccharomyces cerevisiae*", *Yeast*, vol. 3, pp. 175–185 (1987).

Reinikainen et al., "How Do *Trichoderma reesei* cellobiohydrolase bind to and degrade cellulose", *Abstr. Pap. Am. Chem. Soc.*, 202 Meet. Pt. 1 (1991) [Abstract].

Saloheimo et al., "EGIII a new endoglucanase from *Trichoderma reese*: the characterization of both gene and enzyme", *Gene*, vol. 63, pp. 11–22 (1988).

Sambrook et al., *Molecular Cloning A Laboratory Manual*, 2nd Ed., Cold Spring Harbor Laboratory Press, pp. 1.53–1.73 (1989).

Schulein, "Cellulases of *Trichoderma reesei*", *Methods in Enzymology*, vol. 160, pp. 234–242 (1988).

Sheir-Neiss et al., "Characterization of the Secreted Celluloses of *Trichoderma reesei* Wild Type and Mutants During Controlled Permentations", *Appl. Microbiol. Biotechnol.*, vol. 20, pp. 46–53 (1984).

Shoemaker et al., "Molecular Cloning of Exo-cellobiohydrolase I Derived from *Trichoderma reesei* Strain L27", *Biotechnology*, vol. 1, pp. 691 (1983).

Shoemaker et al., "Characterization and Properties of Cellulases Purified from *Trichoderma reesei* Strain L27", *Biotechnology*, pp. 687–690 (1983).

Smith et al., *Curr. Genetics*, vol. 19, pp. 27–33 (1991).

Teeri, "The Cellulolytic Enzyme System of Trichoderma reesei,"*Publications* 38, pp. 13, 17–20 of 1–52–+Appendices (1987).

Teeri et al., "Engineering *Trichoderma* and its cellulases *Trichoderma reesei* cellulase and cellobiohydrolase gene cloning and expression: potential strain and improvement and enzyme engineering" *Trichoderma reesei Cellulases*, pp. 156–167 (1990) [abstract].

Ulker et al., "Characterization of an Unglycosylated Low Molecular Weight 1,4-B-gencanglucanahydrolose of *Trichoderma reesei*", *FEMS Microbiology Letters*, vol. 69, pp. 215–219 (1990).

Van Arsdéll *Bio/Technology* vol. 5, pp. 60–64 (1987).

Voragen et al., "Cellulose of a Mutant Strain of *Trichoderma Uride QM 9414*", *Methods in Enzymology*, vol. 160, pp. 243–251 (1988).

Wilson *Nucl. Acids Res.* vol. 16, pp. 2339–(1988).

Wood "Properties of Cellulolytic Enzyme Systems", *Biochem. Soc. Trans.*, vol. 13, pp. 407–410 (1985).

Wood et al., "Aerobic and Anaerobic Fungal Cellulases, With Special Reference to Their Mode of Attack on Crystalline Cellulose", *Biochemistry and Genetics of Cellulose Degradation*, pp. 31–52 (1988).

Wood et al., "Methods for Measuring Cellulase Activities", *Methods in Enzymology*, vol. 160, pp. 87–112 (1988).

Wood et al., "The Mechanism of Fungal Cellulose Action", *Biochem J.*, vol. 260, pp. 37–43 (1989).

Yamagishi, "Reforming of Cellulosic Fiber With Cellulose", *The Shizuoka Prefectural Hamamatsu Textile Industrial Research Institute Report* vol. 24, pp. 54–61 (1986).

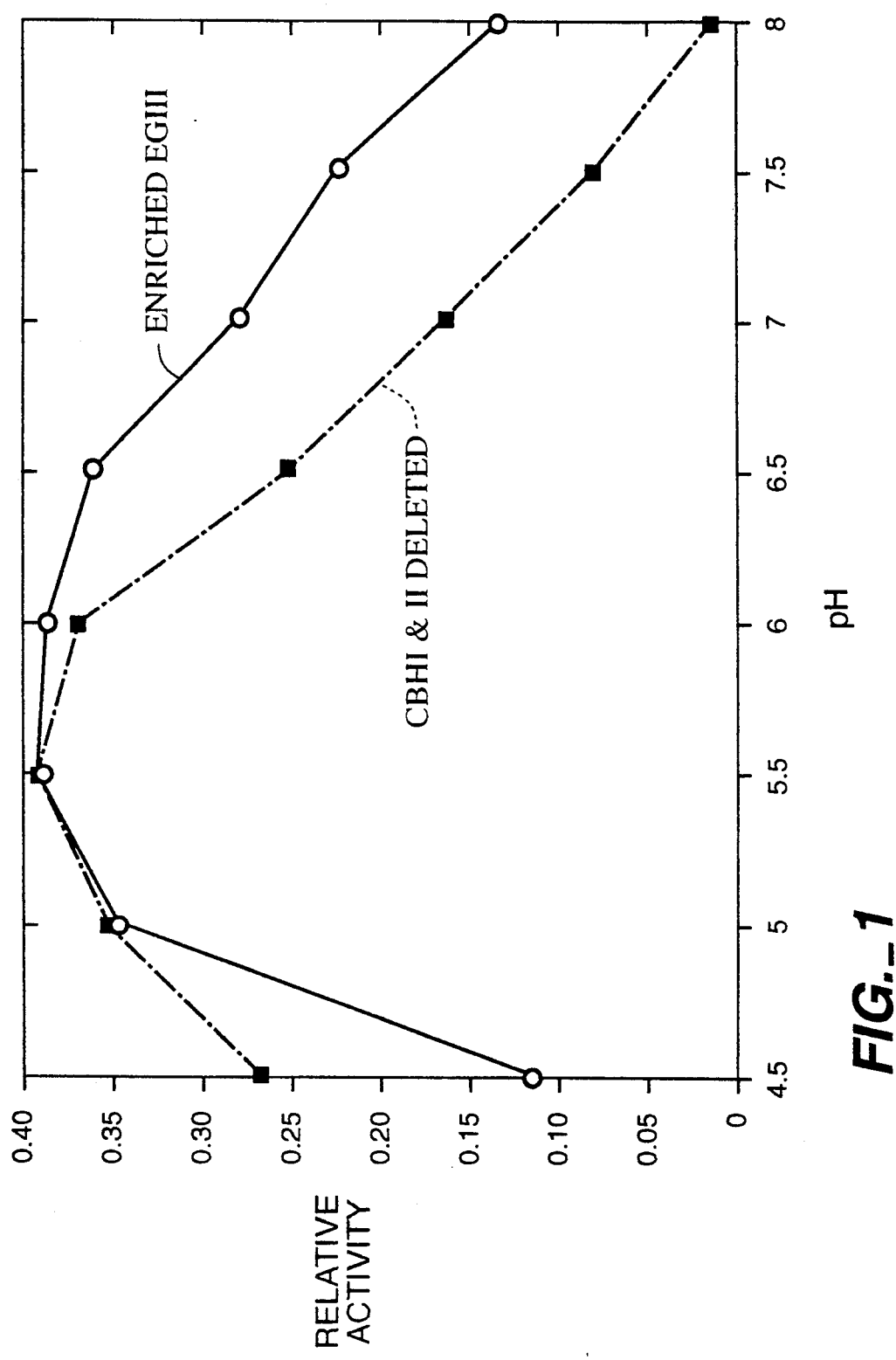
FIG._1

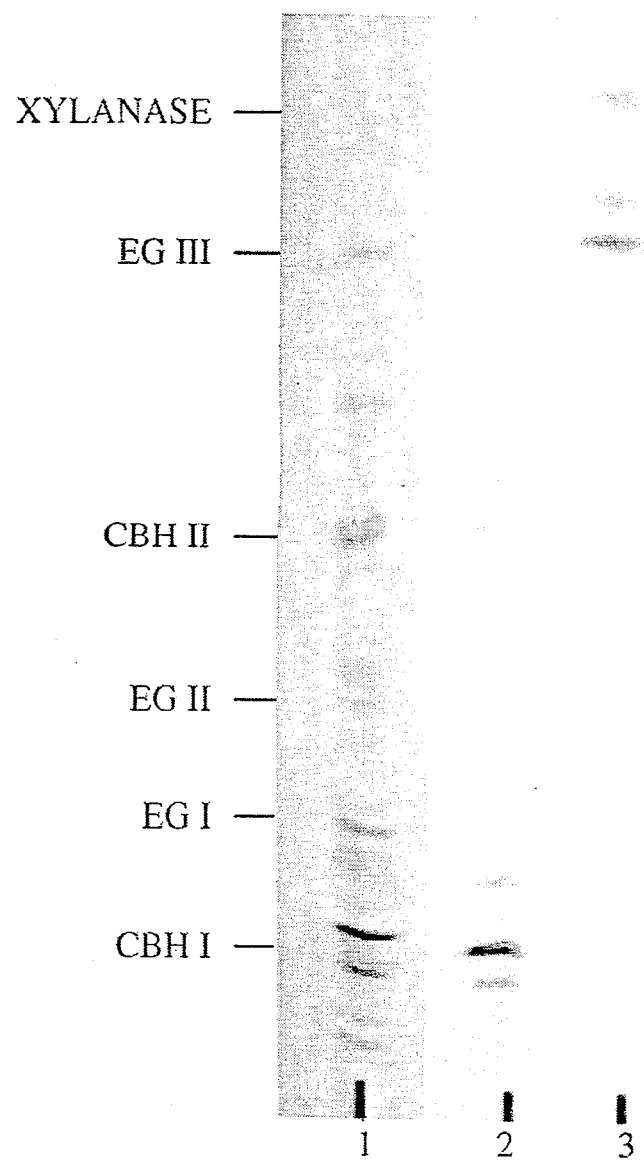
FIG._2
1) IWLGKYGDGPIGSSQGXVNVGGQ
2) PTTASWSYSGSNIRANVAYDLFTAAN
FIG._3

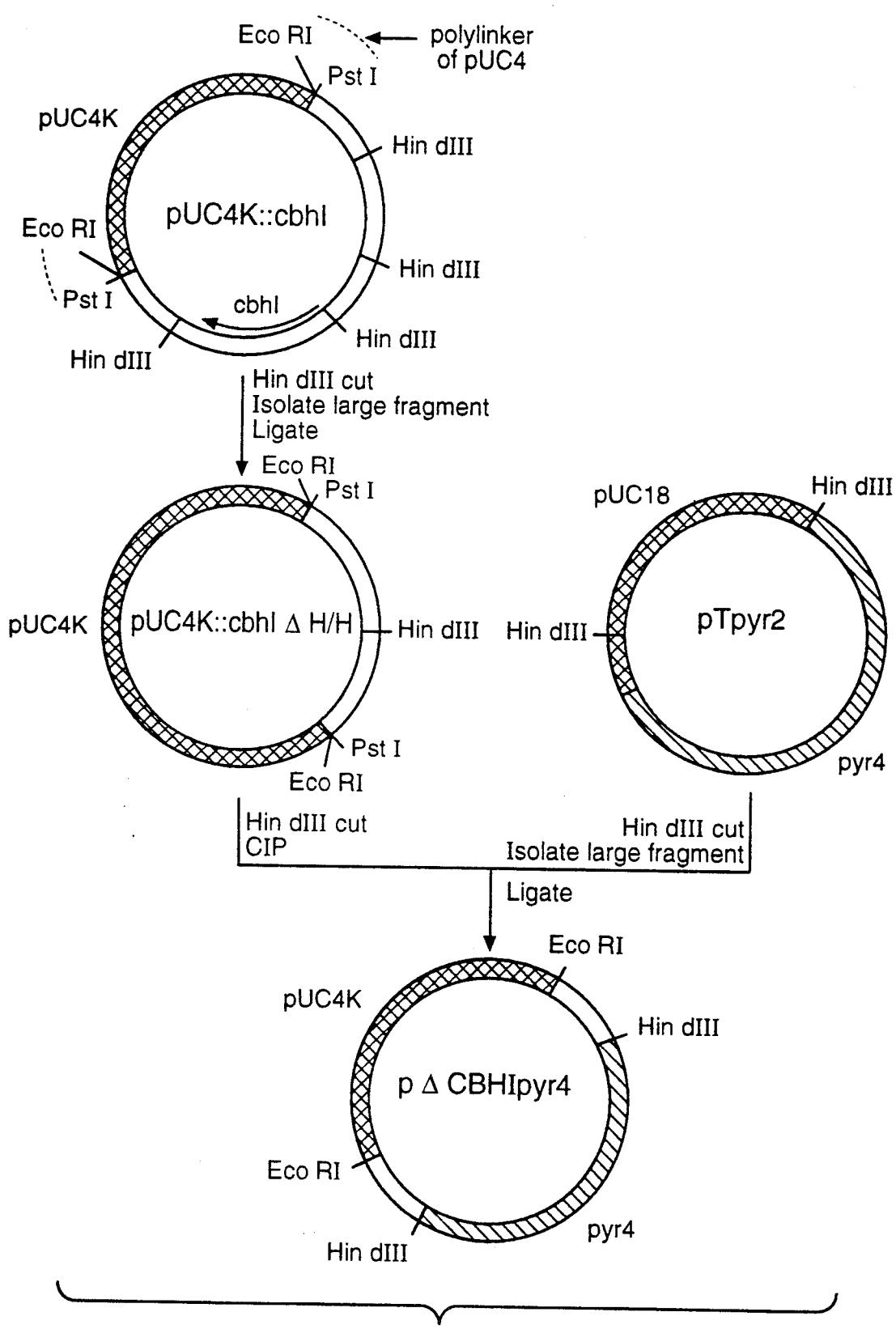
FIG._4

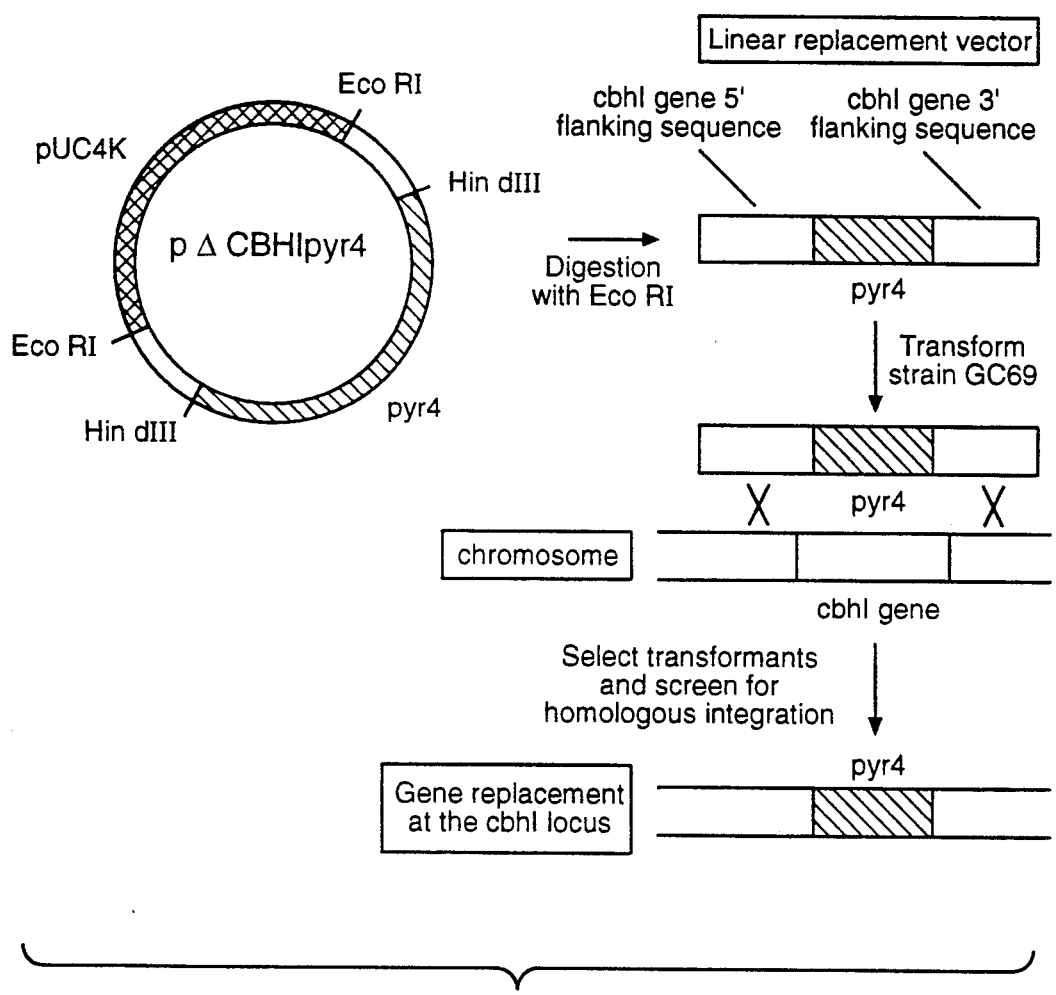
FIG._5

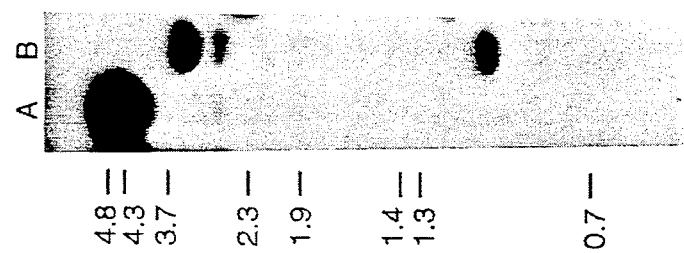
FIG._10
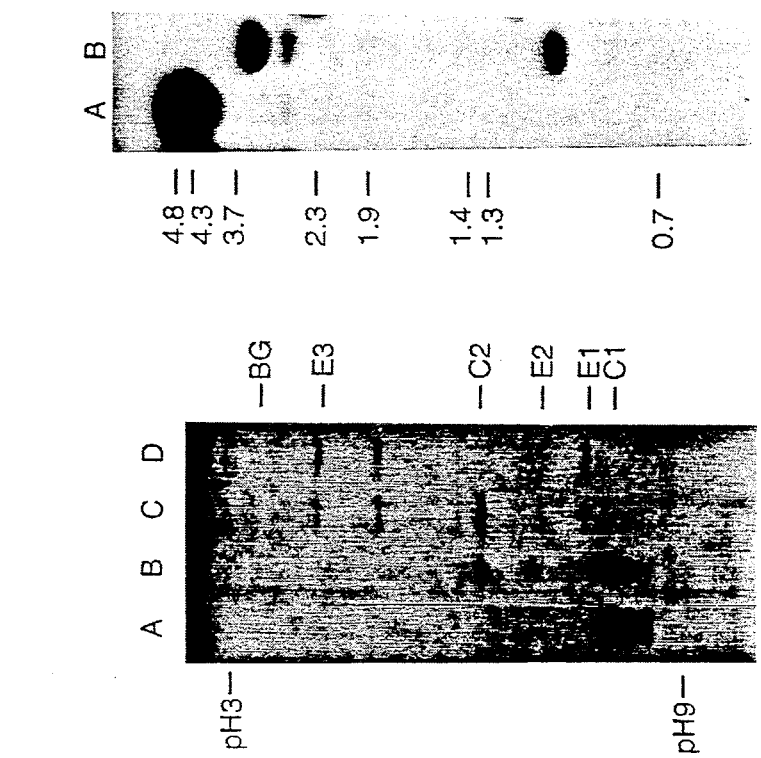
FIG._8
FIG._7
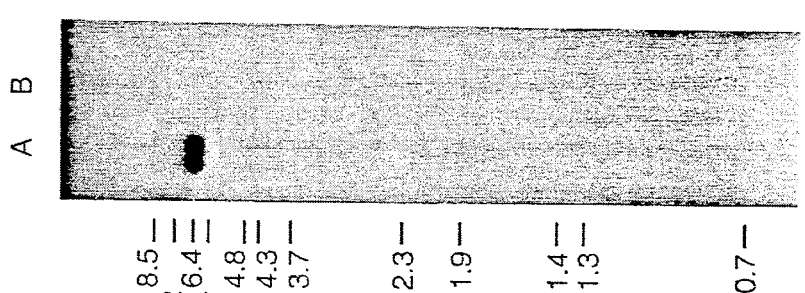
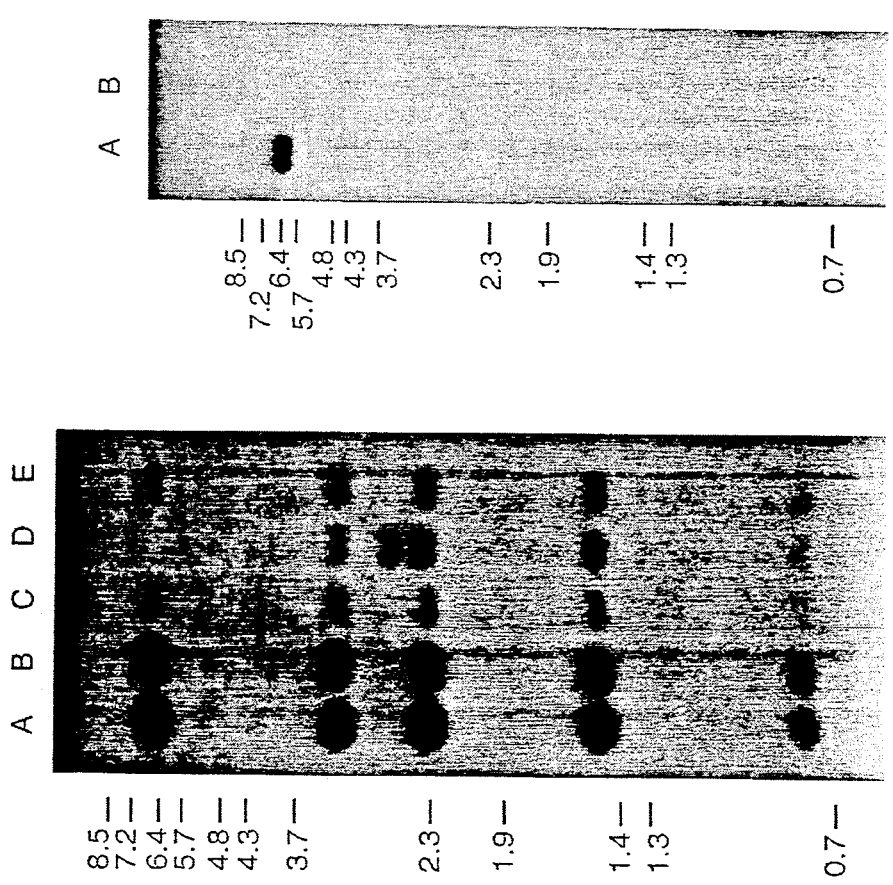
FIG._6

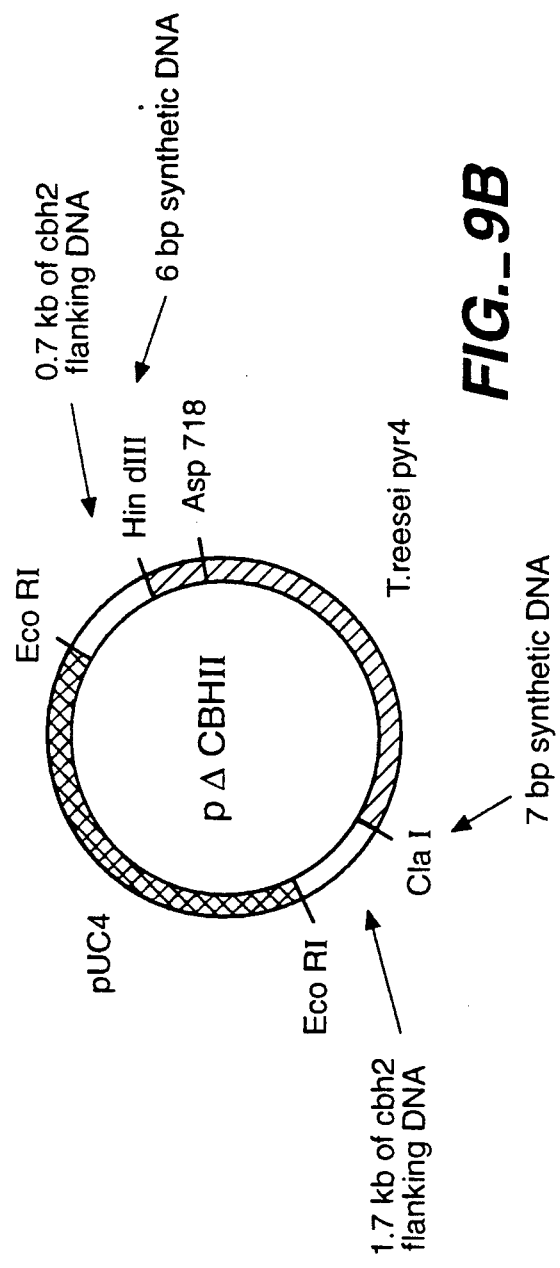
FIG._9A
FIG._9B

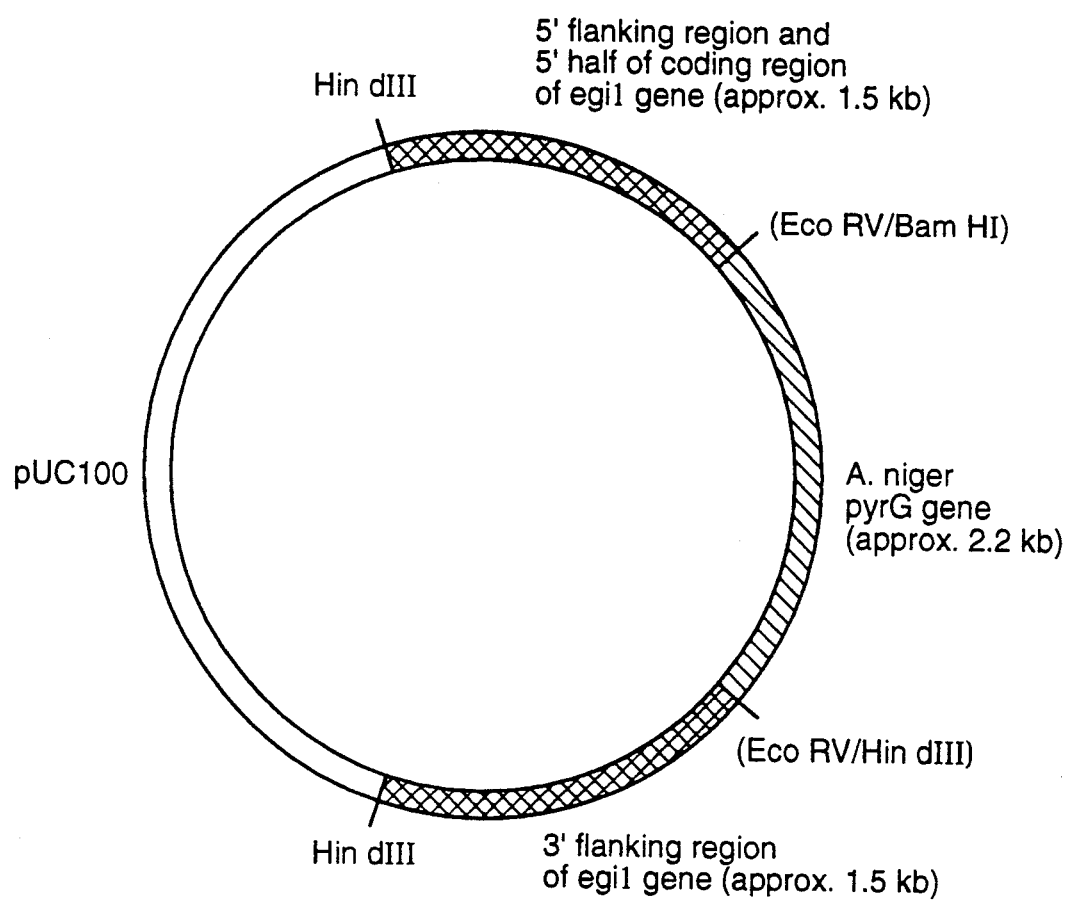
FIG._11

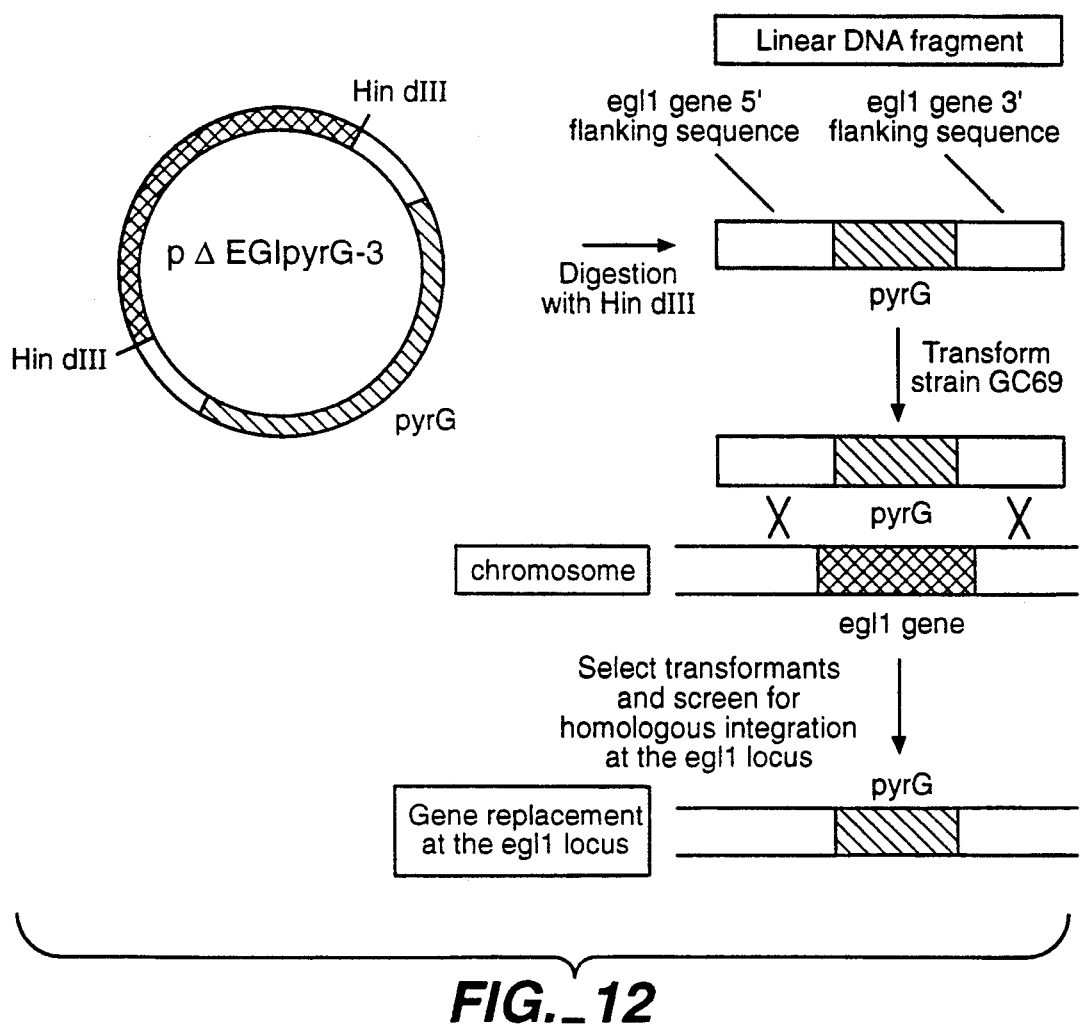
FIG._12

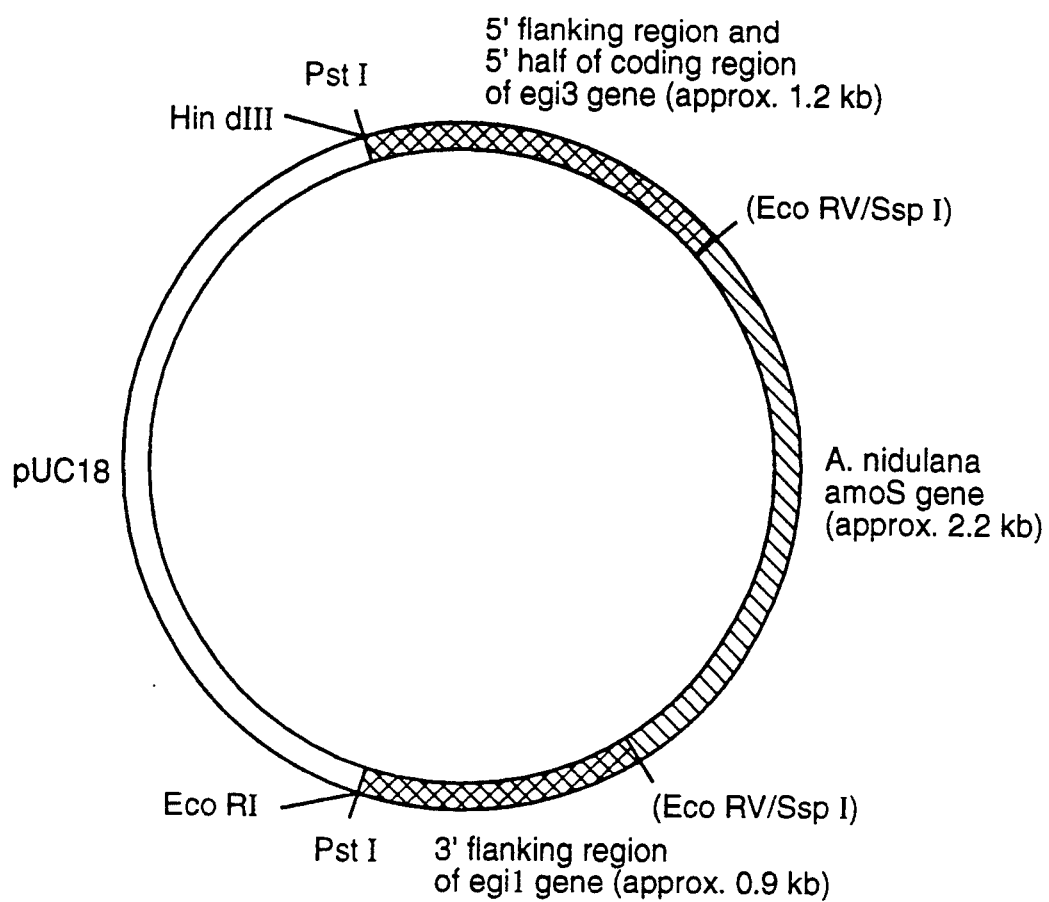
FIG._13

METHODS FOR ISOLATING EG III CELLULASE COMPONENT AND EG III CELLULASE IN POLYETHYLENE GLYCOL USING INORGANIC SALT AND POLYETHYLENE GLYCOL

CROSS-REFERENCE TO RELATED APPLICATIONS

This application is a continuation-in-part of U.S. Ser. No. 07/707,647 filed May 30, 1991, which in turn is a continuation-in-part of U.S. Ser. No. 07/668,640 filed on Mar. 13, 1991 which in turn is a continuation-in-part of U.S. Ser. No. 07/593,919, filed Oct. 5, 1990, now abandoned. This application is a continuation-in-part of 07/770,049 filed Oct. 4, 1991. This application claims priority from International Application No. PCT/US91/07276 filed Oct. 4, 1991. The disclosures of these five applications are incorporated herein in their entirety by reference.

BACKGROUND OF THE INVENTION

1. Field Of the Invention

The present invention is directed to methods for producing a polyethylene glycol solution containing substantially pure EG III cellulase component. In particular, the methods of the present invention are directed in part, to the separation of EG III cellulase component from an aqueous mixture of cellulase proteins containing EG III by the addition of a specified polyethylene glycol to the aqueous mixture to create a two-phase system containing an EG III-rich polyethylene glycol phase and an EG III-poor aqueous phase and separating the EG III-rich phase. The present invention is also directed in part to methods for preparing substantially pure EG III cellulase component by fractionation or by a combination of the above two methods. The present invention is also directed in part, to the enrichment of a xylanase polyethylene glycol phase from an aqueous mixture of cellulase proteins also containing xylanase.

2. State of the Art

Cellulases are known in the art as enzymes that hydrolyze cellulose ($\beta$-1,4-glucan linkages) thereby resulting in the formation of glucose, cellobiose, cellooligosaccharides, and the like. While cellulases are produced (expressed) in fungi, bacteria and the like, cellulase produced by certain fungi and, in particular by the fungus class Trichoderma spp. (especially Trichoderma longibrachiatum), have been given the most attention because a complete cellulase system capable of degrading crystalline forms of cellulose is readily produced in large quantities via fermentation procedures.

In regard to the above, Schulein, "Methods in Enzymology", 160, 25, pages 234 et seq. (1988), disclose that complete fungal cellulase systems comprise several different enzyme classifications including those identified as exo-cellobiohydrolases (EC 3.2.1.91) ("CBH"), endoglucanases (EC 3.2.1.4) ("EG"), and $\beta$-glucosidases (EC 3.2.1.21) ("BG"). The fungal cellulase classifications of CBH, EG and BG can be further expanded to include multiple components within each classification. For example, multiple CBHs and EGs have been isolated from a variety of fungal sources.

The complete cellulase system comprising CBH, EG and BG components is required t0 efficiently convert crystalline cellulose to glucose. Isolated components are far less effective, if at all, in hydrolyzing crystalline cellulose. Moreover, a synergistic relationship is observed between the cellulase components particularly if they are of different classification.

On the other hand, cellulases and components thereof, used either singularly or in combination, are also known in the art to be useful in detergent compositions. For example, endoglucanase components of fungal cellulases have been used for the purposes of enhancing the cleaning ability of detergent compositions, for use as a softening agent, and for use in improving the feel of cotton fabrics, and the like. However, there is a problem with using the EG I and EG II components derived from Trichoderma spp. and especially Trichoderma longibrachiatum in detergent compositions. Specifically, such components have their maximal activity at acidic pHs whereas most laundry detergent compositions are formulated for use at neutral or alkaline (pH $>7$ to about 10) conditions. While it is disclosed in U.S. Ser. No. 07/668,640 that the use of one or more acidic endoglucanase components of Trichoderma longibrachiatum in detergent compositions will provide improvements in softening, color retention/restoration and feel to cotton-containing fabrics even when treated under alkaline conditions, it is disclosed in U.S. Ser. No. 07/707,647 that the EG III component of Trichoderma spp. provides for superior and unexpected advantages in detergent compositions as compared to the EG I and EG II components of Trichoderma longibrachiatum.

Specifically, the EG III cellulase component has been found to possess significant enzymatic activity under alkaline conditions and is particularly suited for use in laundry conditions where a neutral or alkaline detergent wash medium is employed.

In addition to its use in laundry detergents, the substantially pure EG III cellulase component described herein can additionally be used in a pre-washing step in the appropriate solution at an intermediate pH where sufficient activity exists to provide desired improvements in color retention/restoration, softening and feel as disclosed in U.S. Ser. No. 07/707,647 filed May 30, 1991 and incorporated herein by reference.

Also, it is contemplated that the substantially pure EG III cellulase component described herein can be used in home use as a stand alone composition suitable for restoring color to faded fabrics (see, for example, U.S. Pat. No. 4,738,682, which is incorporated herein by reference in its entirety) as well as used in a spot-remover.

Additionally, it is further contemplated that the high activity under neutral to alkaline conditions of the EG III cellulase component would be beneficial in textile processes for treating cotton-containing fabrics (see U.S. Ser. Nos. 07/677,385 and 07/678,865 which are incorporated herein by reference in their entirety) as well as in silage and/or composting processes.

In contrast to the above, this invention is directed to efficient processes for the separation and purification of the EG III cellulase component from aqueous enzyme mixtures, particularly from a complete fungal cellulase composition and particularly for commercial scale production of the EG III cellulase component.

SUMMARY OF THE INVENTION

Specifically, the present invention is directed to methods for producing a polyethylene glycol solution containing substantially pure EG III cellulase component from an aqueous mixture containing cellulase proteins including EG III cellulase component. Accordingly, in one of its method aspects, the present invention is directed to a method for selectively recovering EG III from an aqueous mixture containing cellulase proteins including EG III cellulase, which method comprises the addition to the aqueous mixture of an effective amount of polyethylene glycol (PEG) in the presence of a inorganic salt. The mixture forms a two phase liquid mixture containing an EG III-rich polyethylene glycol phase and an EG III-poor aqueous phase. In this embodiment, the EG III-rich phase is substantially free of other cellulase proteins and is then separated.

The methods of the present invention are also directed in part, to the isolation of substantially pure xylanase from an aqueous mixture of cellulase proteins also containing xylanase by addition to the aqueous mixture of an effective amount of polyethylene glycol in the presence of an inorganic salt. When the aqueous mixture also contains EG III, the recovered polyethylene glycol phase contains both EG III and xylanase.

In another method, the present invention is directed to selectively recovering EG III cellulase from an aqueous cellulase protein mixture including EG III, which method comprises applying the aqueous mixture to an anion exchange column. The protein fraction not bound to the anion exchange column contains the EG III component. This fraction is then applied to a cation exchange column, which binds the EG III cellulase, which is later eluted from the resin with a salt solution.

A third preferred method of this invention is a combination of the above two methods in either order.

The aqueous cellulase protein mixture can be a whole cell extract or, more preferably, a whole cellulase composition from a wild-type *Trichoderma spp.* strain, a genetically modified *Trichoderma spp*, strain or any other aqueous mixture containing cellulase proteins including EG III which is compatible with the methods of this invention.

BRIEF DESCRIPTION OF THE DRAWINGS

FIG. 1 illustrates the RBB-CMC activity profile over a pH range at 40° C. for an EG enriched fungal cellulase composition derived from a strain of *Trichoderma longibrachiatum* transformed so as to be incapable of expressing CBH I and CBH II; as well as the activity profile of an enriched EG III cellulase composition derived from *Trichoderma longibrachiatum* over a pH range at 40° C.

FIG. 2 is an isoelectric focusing gel which, in Lane 1, displays the proteins expressed by a wild type *Trichoderma longibrachiatum*; in Lane 2 displays the proteins expressed by a strain of *Trichoderma longibrachiatum* transformed so as to be incapable of expressing EG I and EG II components; and in Lane 3 displays the proteins found in substantially pure EG III cellulase similar to that obtained by the method of Example 1. The right hand margin of this Figure is marked so as to identify the bands attributable to CBH I, CBH II, EG I, EG II, EG III and xylanase.

FIG. 3 is the amino acid sequence obtained from two fragments of EG III (SEQ ID NOS: 1 and 2).

FIG. 4 is an outline of the construction of pΔCBHIpyr4.

FIG. 5 illustrates deletion of the *T. reesei* gene by integration of the larger EcoRI fragment from pΔCBHIpyr4 at the cbh1 locus on one of the *T. reesei* chromosomes.

FIG. 6 is an autoradiograph of DNA from *T. reesei* strain GC69 transformed with EcORI digested pΔCBHIpr4 after Southern blot analysis using a $^{32}$P-labelled pΔCBHIpyr4 as the probe. The sizes of molecular weight markers are shown in kilobase pairs to the left of the Figure.

FIG. 7 is an autoradiograph of DNA from a *T. longibrachiatum* strain GC69 transformed with EcoRI digested pΔCBHIpyr4 using a $^{32}$P-labelled pIntCBHI as the probe. The sizes of molecular weight markers are shown in kilobase pairs to the left of the Figure.

FIG. 8 is an isoelectric focusing gel displaying the proteins secreted by the wild type and by transformed strains of *T. longibrachiatum*. Specifically, in FIG. 8, Lane A of the isoelectric focusing gel employs partially purified CBHI from *T. longibrachiatum*; Lane B employs a wild type *T. longibrachiatum*: Lane C employs protein from a *T. longibrachiatum* strain with the cbh1 gene deleted; and Lane D employs protein from a *T. longibrachiatum* strain with the cbh1 and cbh2 genes deleted. In FIG. 8, the right hand side of the figure is marked to indicate the location of the single proteins found in one or more of the secreted proteins. Specifically, BG refers to the β-glucosidase, E1 refers to endoglucanase I, E2 refers to endoglucanase II, E3 refers to endoglucanase III, C1 refers to exo-cellobiohydrolase I and C2 refers to exocellobiohydrolase II.

FIG. 9A is a representation of the *T. longibrachiatum* cbh2 locus, cloned as a 4.1 kb EcoRI fragment on genomic DNA and FIG. 9B is a representation of the cbh2 gene deletion vector pPΔCBHII.

FIG. 10 is an autoradiograph of DNA from *T. longibrachiatum* strain P37PΔCBHIPyr-26 transformed with EcoRI digested pPACBHII after Southern blot analysis using a $^{32}$p labelled pPΔCBHII as the probe. The sizes of molecular weight markers are shown in kilobase pairs to the left of the Figure.

FIG. 11 is an outline of the construction of pΔEGI-pyrG-3.

FIG. 12 illustrates deletion of the egl1 gene by integration of the HindIII fragment from pΔΔEGIpyrG-3 at the egl1 locus on one of the *T. longibrachiatum* chromosomes.

FIG. 13 is an outline of the construction of pAΔE-GII-1.

DETAILED DESCRIPTION OF THE INVENTION

As noted above, the present invention generally relates to methods for producing a substantially pure EG III cellulase component whether in a polyethylene glycol solution or as a recovered protein.

However, prior to discussing this invention in further detail, the following terms will first be defined:

1. Definitions

As used herein the following terms have the following meanings:

"EG III cellulase" refers to the endoglucanase component derived from *Trichoderma spp.* or any microorganism producing a protein equivalent to EG III produced by Trichoderma spp. characterized by a pH optimum of about 5.5 to 6.0, an isoelectric point (pI) of from about 7.2 to 8.0, and a molecular weight of about 23 to 28 Kdaltons. Preferably, EG III cellulase is derived from either *Trichoderma longibrachiatum* or from *Trichoderma viride*. EG III cellulase derived from *Trichoderma longibrachiatum* has a pH optimum of about 5.5 to 6.0, an isoelectric point (pI) of about 7.4 and a molecular weight of about 25 to 28 Kdaltons. EG III cellulase derived from *Trichoderma viride* has a pH optimum of about 5.5, an isoelectric point (pI) of about 7.7 and a molecular weight of about 23.5 Kdaltons. Additionally, it is contemplated that the amino acid sequence of the EG III cellulase may be altered. Alteration of the active sites on this enzyme may lead to a variety of different changes such as different pH optima, different temperature optima or altered affinities for the substrate.

Because of its high pI, the EG III component is found in a region of an isoelectric focusing gel where high pI xylanases and other high pI components expressed by Trichoderma spp. are generally found. In fact, it has been hypothesized in the literature that the band identified as EG III in FIG. 2 was a degradation product of either EG I or II. However, gel isoelectric focusing of EG I and EG II deleted cellulase (prepared in the manner of U.S. Ser. Nos. 07/770,049 and 07/668,640) demonstrated that this band was not attributable to a degradation product of either EG I or II. (See FIG. 2).

It is noted that EG II has been previously referred to by the nomenclature "EG III" by some authors but current nomenclature uses the term "EG II". In any event, the EG II protein is substantially different from the EG III protein in its molecular weight, pI, and pH optimum as evidenced by Table 2 of Example 2 presented below.

"Substantially pure EG III cellulase" refers to a composition, solid or liquid, of cellulase proteins containing at least 50 weight percent, more preferably at least 70 weight percent and most preferably at least 90 weight percent of EG III cellulase component based on the total weight of cellulase proteins.

"Substantially free of all other cellulase proteins," refers to a composition in which at least 50 weight percent, more preferably 60 weight percent and most preferably at least 90 weight percent of the cellulase proteins, other than EG III, have been removed from the original aqueous mixture of cellulase enzymes.

"Enriched in xylanase" refers to an aqueous solution or composition, or polyethylene glycol phase containing an increase in xylanase concentration by the processes of this invention by at least a factor of 4, more preferably by at least a factor of 10.

"Cellulase proteins" refer to cellulase proteins which contain any and all exo-cellobiohydrolase (CBH) proteins, endoglucanase (EG) proteins and $\beta$-glucosidase (BG) proteins derived from wild-type fungal sources or microorganisms genetically modified so as to incorporate and express all or part of the cellulase genes obtained from a wild-type fungal sources. Collectively, all of such proteins (i.e., CBH, EG and BG proteins) are referred to as "cellulase proteins". Contrarily, cellulase proteins do not include other proteins expressed by Trichoderma spp. including xylanases, proteases, amylases, etc.

"Endoglucanase (EG) components" refer to the EG components of Trichoderma spp. including the EG I, EG II and/or EG III components of *Trichoderma longibrachiatum*. The endoglucanase components of Trichoderma spp. (e.g., the EG I, EG II, EG III, of *T. longibrachiatum*), either alone or in combination, impart improved feel, improved appearance, softening, color enhancement, and/or a stone washed appearance to cotton-containing fabrics (as compared to the fabric prior to treatment) when these components are incorporated into a textile treatment medium and the fabric is treated with this medium. In addition to the above, EG III possesses substantial activity at alkaline pHs where many detergent compositions are employed.

"Exo-cellobiohydrolase ("CBH") components" refer to the CBH components of Trichoderma spp. including the CBH I and CBH II components of *Trichoderma longibrachiatum*. When used in the absence of the EG components of Trichoderma spp., the CBH components of Trichoderma spp. alone do not impart significant color retention/restoration and improved feel to the so-treated cotton-containing fabrics. Additionally, when used in combination with such EG components, the CBH 1 component of *Trichoderma longibrachiatum* can impart enhanced strength loss and incremental cleaning benefits to cotton-containing fabrics.

"$\beta$-Glucosidase (BG) components" refer to those components of cellulase which exhibit BG activity; that is to say that such components will act from the non-reducing end of cellobiose and other soluble cellooligosaccharides ("cellobiose") and give glucose as the sole product. BG components do not adsorb onto or react with cellulose polymers. Furthermore, such BG components are competitively inhibited by glucose ($K_i$ approximately 1 mM). While in a strict sense, BG components are not literally cellulases because they cannot degrade cellulose, such BG components are included within the definition of the cellulase system because these enzymes facilitate the overall degradation of cellulose by further degrading the inhibitory cellulose degradation products (particularly cellobiose) produced by the combined action of CBH components and EG components. Without the presence of BG components, moderate or little hydrolysis of crystalline cellulose will occur. BG components are often characterized on aryl substrates such as p-nitrophenol B-D-glucoside (PNPG) and thus are often called aryl-glucosidases. It should be noted that not all aryl-glucosidases are BG components, in that some do not hydrolyze cellobiose.

2. Methodology

A. Recovery of EG III with Polyethylene Glycol

The present invention is directed in part to the discovery that EG III cellulase substantially free of other cellulase proteins can be obtained from an aqueous mixture of cellulase proteins containing EG III by the addition of a specified polyethylene glycol. Surprisingly, under these conditions substantially all of the cellulase proteins, other than EG III, remain in the aqueous phase whereas the EG III is recovered in the polyethylene glycol phase in substantially pure quantities. It has also been found that under these conditions, enriched quantities of xylanase are recovered in the polyethylene glycol phase.

In one preferred method of carrying out the present invention, an aqueous mixture containing cellulase was filtered to remove cell debris and other solids and produced a liquid filtrate containing a mixture of proteins including cellulase proteins. More preferably a cell-free cellulase protein mixture, such as CYTOLASE 123 (commercially available from Genencor International, Inc., South San Francisco, Calif.) is used. In another method the aqueous mixture could be obtained from any compatible source including compatible aqueous mixtures already enriched for EG III, more particularly any of the EG III solutions described in concurrently filed application, U.S. Ser. No. 07/862,641, entitled "Methods for Producing Substantially Pure EG III Cellulase Using Alcohol," which is incorporated herein in its entirety.

After the filtrate is obtained from the filtration step, an inorganic salt may be added to the filtrate before contacting the filtrate with the polyethylene glycol (PEG). In some cases, the addition of inorganic salts may enhance the partition of the EG III cellulase component from the aqueous phase into the polyethylene glycol phase.

The polyethylene glycol is then mixed with the aqueous mixture for a period of time sufficient to effect transfer of substantial quantities of EG III to the polyethylene glycol phase. The specific period of time will vary depending on the amount of polyethylene glycol added, the amount of salt added, and the like. Such factors are readily ascertained by the skilled artisan. However, in a preferred embodiment, the polyethylene glycol is mixed with the aqueous mixture for at least about 2 hours, more preferably about 4 hours, and most preferably about 18 hours. The polyethylene glycol aqueous mixture is allowed to settle after mixing for a period of time sufficient to effect phase separation and preferably for at least about 4 hours, more preferably 8 hours, most preferably about 18 hours. A two-phase liquid mixture is formed. The EG III cellulase component is present in the polyethylene glycol phase. The polyethylene glycol EG III-rich phase is then separated from the aqueous phase. The recovered EG III-rich solution contains a mixture of cellulase protein wherein from about 50 to greater than 90 weight percent of these proteins are EG III.

The EG III component can be purified from the polyethylene glycol phase by a variety of methods. In a preferred embodiment, the EG III cellulase component is precipitated with cold ethanol and resuspended in a desired aqueous solution. Suitable buffers are buffers known in the art which do not denature the EG III cellulase component such as 50 mM sodium acetate, pH 5, or 10 mM citrate phosphate, pH 5.

One of the essential features of this aspect of the invention is the use of polyethylene glycol (PEG). The PEG has been found to be uniquely active and selective for recovering EG III cellulase from aqueous mixtures containing other cellulase proteins. In this regard, an "effective amount of polyethylene glycol" is that amount added to the aqueous mixture which is necessary to selectively partition a sufficient amount of the EG III component but not the other cellulase proteins. The amount of polyethylene glycol added is preferably from about 0.5% wt/v. to 10% wt/v., more preferably 4% wt/v. The average molecular weight of PEG used in the method of this invention is from about 5,000 to 10,000, preferably from about 7,000 to 9,000 and most preferably about 8,000.

Regarding the above procedure, use of a polyethylene glycol having a molecular weight substantially less than about 5,000 gave reduced separation from the other cellulase enzymes; whereas, use of polyethylene glycol having a molecular weight substantially greater than about 10,000 resulted in reduced capture of the EG III cellulase component from the PEG phase. In a preferred embodiment, the molecular weight of the polyethylene glycol is about 8,000.

The polyethylene glycol has been found to be particularly useful in separating the EG III cellulase component from an aqueous mixture of cellulase proteins because the aqueous mixture contains a high percentage of other cellulase proteins relative to the percentage of EG III. The normal distribution of cellulase proteins in the CYTOLASE 123 cellulase system is as follows:

| CBH I | 45-55 weight percent |
| CBH II | 13-15 weight percent |
| EG I | 11-13 weight percent |
| EG II | 8-10 weight percent |
| EG III | 1-4 weight percent |
| BG | 0.5-1 weight percent |

Useful quantities of EG III component are obtained by the methods of this invention. The loss of recovery of the EG III component by the PEG extraction methods of this invention as compared to other methods is compensated for by the speed of recovery of the EG III component. The procedure does not require extensive fractionation steps for purification, although such steps can be followed for further purification, if desired.

The term "inorganic salt" means a compatible inorganic salt having a sulfate or phosphate ion which when used in conjunction with the polyethylene glycol facilitates purification of EG III without denaturing the protein. Such inorganic salts include by way of example, sodium sulfate, magnesium sulfate, ammonium sulfate, sodium phosphate and potassium phosphate. An "effective amount of inorganic salt" is that amount which when added to an aqueous mixture containing polyethylene glycol will result in the preferential separation of the EG III component into the polyethylene glycol phase and the retention of the cellulase proteins, other than EG III, in the aqueous phase.

The concentration of the inorganic salts can be varied to provide the desired result. It has been found that the EG III cellulase component is sequestered in the PEG phase best in the presence of a concentrated salt solution of from about 4% to 20% wt/vol, more preferably a concentrated salt solution of 10% to 14% wt/vol. It has been found that salt levels substantially greater than about 20% wt/vol caused precipitation problems; whereas, salt levels substantially less than about 4% wt/vol gave poor separation or the solution remained in a single phase.

B. Recovery of EG III Cellulase by Fractionation

In another preferred method of carrying out the process of the present invention, EG III is recovered from a filtered aqueous mixture containing cellulase proteins, such as CYTOLASE 123 cellulase, by fractionation. Such fractionation can be achieved by desalting the aqueous mixture at appropriate stages using an appropriate desalting resin and separating EG III by using a cation exchange resin and anion exchange resin. Specifically, EG III has been recovered by first desalting the aqueous mixture with a Sephadex G-25 gel filtration resin column using 10 mM sodium phosphate buffer at pH 6.8. The desalted solution, is then loaded onto a QA Trisacryl M anion exchange resin column. The fraction not bound on this column contains EG III. This fraction is desalted using a Sephadex G-25 gel filtration resin column equilibrated with 10 mM sodium citrate, pH 4.5. This solution is loaded onto a SP Trisacryl M cation exchange resin column. The EG III cellulase component is eluted with an aqueous solution of 200 mM sodium chloride.

In another preferred method of carrying out the process of the present invention, the EG III sample obtained from the cation exchange column can be further fractionated. The EG III sample is desalted with a Sephadex G-25 column which had been previously equilibrated with 10 mM sodium citrate pH 4. The solution was applied to a FPLC system using a Mono-S-HR 5/5 column (available from Pharmacia LKB Biotechnology, Piscataway, N.J.). The column is then eluted with 0–200 mM aqueous gradient of sodium chloride at a rate of 0.5 ml/minute. The EG III cellulase component was recovered and was determined to be greater than 90% pure by gel electrophoresis. EG III of this purity is suitable for determining the N-terminal amino acid sequence by known techniques.

Sepharose resins are a well-known class of resins. As used herein, "sepharose" refers to any sepharose resin having a sufficient exclusion size to retain the salt but exclude the EG III. As used herein, an "anion exchange resin" refers to any resin having cationic functional groups providing sufficient charge density to bind at least some of the cellulase proteins other than EG III at a pH below the pH of EG III. Suitable anionic resins contain aminoethyl (AE), diethylaminoethyl (DEAE) and quaternary aminoethyl (QAE) functional groups. As used herein, a "cation exchange resin" refers to any resin containing anion functional groups providing sufficient charge density to bind EG III at a pH below the pI of EG III. Suitable compatible cationic resins contain sulphopropyl (SP), phospho (P) and carboxymethyl (CM) functional groups.

It may be desirable for the EG III cellulase components described above to be further purified. For example, the EG III cellulase component isolated in the procedures described above can be further purified by utilizing material obtained from the first PEG extraction procedure in the second fractionation procedure, or vice versa.

The EG III recovered herein can also be further purified by the methods recited in U.S. Ser. No. 07/862,641, filed concurrently herewith and entitled METHODS FOR PRODUCING SUBSTANTIALLY PURE EG III CELLULASE USING ALCOHOL which application is incorporated herein by reference in its entirety.

It will be recognized that the above descriptions are preferred methods of carrying out the process of the present invention and that numerous variations of the above methods can be made in the process following the teachings of this invention. The various process conditions can be altered and reagents used can be changed to provide various desired or optimum operating conditions for recovery of the EG III cellulase component from any suitable aqueous mixture of enzymes containing the EG III component.

As will be recognized by those skilled in the art, the acids, bases and salts referred to above in the description of the process of this invention can be changed or substituted with equivalent acids, bases or salts which provide the desired pH or the desired salt content without interfering with the operation of the invention and which do not denature the EG III cellulase component.

Additionally, the fractionation method of this invention can be preceded by the extraction method of this invention or vice versa. The aqueous mixture can be extracted with polyethylene glycol so as to provide for an initial polyethylene glycol EG III-rich phase (about 50–90% pure EG III) which can then be further purified by the fractionation method of this invention to provide for an aqueous solution containing substantially pure EG III cellulase.

EG III cellulase can be purified from any source including strains of Trichoderma spp. which produces EG III under suitable fermentation conditions. While the particular source of EG III is not critical, preferred sources are *Trichoderma longibrachiatum* and *Trichoderma viride*. A particularly preferred source of EG III from *Trichoderma longibrachiatum* is Cytolase 123 cellulase which is commercially available from Genencor International, Inc., 180 Kimball Way, South San Francisco, Calif. 94080. Procedures suitable for obtaining substantially pure EG III cellulase from a complete cellulase system derived from Trichoderma spp. ("whole cellulase") include those recited in the examples set forth herein below. These examples demonstrate that substantially pure EG III cellulase is readily obtained by subjecting whole cellulase either to PEG extraction and/or to repeated fractionation steps utilizing different fractionation materials (columns).

In order to enhance the efficiency of the isolation of EG III, it may be desirable to employ a microorganism (e.g., *Trichoderma longibrachiatum*) genetically modified so as to overexpress EG III and/or to be incapable of producing one or more of EG I, EG II, CBH I and/or CBH II components. This will necessarily lead to more efficient isolation of EG III by, for example, fractionation and/or PEG extraction as described above. Production of some of these strains of *Trichoderma longibrachiatum* are disclosed in U.S. Ser. No. 07/668,640, filed Mar. 13, 1991 and in the Examples below.

Additionally, it is contemplated that substantially pure EG III cellulase can be prepared by genetically modifying microorganisms so as to produce substantially pure EG III cellulase. For example, substantially pure EG III prepared by fractionation methods set forth in the Examples below was employed to determine the amino acid sequence of parts of the protein using known sequencing methods (Example 4). This information can be used to prepare synthetic DNA probes in order to clone the gene encoding the EG III cellulase component. Once the EG III gene is cloned, it could be manipulated by recognized techniques and ultimately inserted into various Trichoderma spp. strains or into other microorganisms. See, for example, U.S. Ser. No. 07/770,049, filed Oct. 4, 1991 and which is a continuation-in-part of U.S. Ser. No. 07/593,919, filed Oct. 5, 1990 and U.S. Ser. No. 07/668,640, filed Mar. 13, 1991, both of which disclose methods for genetically engineering *Trichoderma longibrachiatum* so that the modified microorganism is incapable of expressing one or more of the cellulase genes and, in fact, may overproduce another cellulase gene. The disclosures of U.S. Ser. No 07/770,049, filed Oct. 4, 1991, U.S. Ser. No. 07/593,919, filed Oct. 5, 1990, and U.S. Ser. No. 07/668,640, filed Mar. 13, 1991, are incorporated herein by reference in their entirety.

Using the methods described in these applications, *Trichoderma longibrachiatum* can be genetically manipulated so as to produce EG III with or without other cellulase proteins. Moreover, the methods described in these applications create *Trichoderma longibrachiatum* strains which do not produce any heterologous proteins.

Additionally, it would be possible to express the EG III-encoding gene in other microorganisms, including, but not limited to, yeast species such as *Saccharomyces cerevisiae, Pichia pastoris, Hansenula polymorpha, Kluyveromyces lactis, Yarrowia lipolytica, Schanniomyces occidentalis*, etc. See, for example, PCT application Publication No. WO 85/04672. In order to obtain expression in these alternative, non-Trichoderma hosts, it may be necessary to functionally combine the EG III-coding DNA sequence with promoter and terminator sequences obtained from a gene from that particular host. It may also be necessary to substitute the DNA sequence encoding a secretion signal sequence from the alternative host for the DNA sequence encoding the EG III secretion signal sequence. Production and secretion of EG III in other organisms could enable EG III to be obtained in substantially pure form.

The substantially pure EG III cellulase described above can be further processed into a liquid diluent, granules, emulsions, gels, pastes, or the like. Such forms are well known to the skilled artisan. When a solid detergent composition is desired, the cellulase composition is preferably formulated as granules. Preferably, the granules can be formulated so as to contain a cellulase protecting agent. See, for instance, U.S. Ser. No. 07/642,669 filed Jan. 17, 1991 and entitled "GRANULES CONTAINING BOTH AN ENZYME AND AN ENZYME PROTECTING AGENT AND DETERGENT COMPOSITIONS CONTAINING SUCH GRANULES" which application is incorporated herein by reference in its entirety. Likewise, the granules can be formulated so as to contain materials to reduce the rate of dissolution of the granule into the wash medium. Such materials and granules are disclosed in U.S. Ser. No. 07/642,596 filed on Jan. 17, 1991 as and entitled "GRANULAR COMPOSITIONS" which application is incorporated herein by reference in its entirety. The granules or other detergent formulations containing EG III can then be used for cleaning fabrics, imparting softening properties to the fabric and the like.

The following examples are offered to illustrate the present invention and should not be construed in any way as limiting the scope of this invention.

EXAMPLES

Example 1

Large Scale Extraction of EG III Cellulase Enzyme

A. One hundred liters of cell free cellulase filtrate were heated to about 30° C. The heated material was made about 4% wt/vol Carbowax TM PEG 8000 (polyethylene glycol, average MW of about 8000) (Union Carbide, Danbury, Conn.) and about 10% wt/vol anhydrous sodium sulfate. The mixture formed a two phase liquid mixture. The phases were separated using an SA-1 disk stack centrifuge. The phases were analyzed using silver staining isoelectric focusing gels. Fractionation and enrichment were obtained for EG III and xylanase. The recovered composition contained about 20 to 50 weight percent of EG III. The amount of xylanase recovered in the polyethylene glycol phase represents enrichment of the xylanase by a factor of at least 4.

B. One hundred litres of cell-free cellulase filtrate were added to a 130 liter container with a cone bottom and an outlet at bottom center. The starting material can be whole cellulase or cellulase from strains which have been deleted for cellulases other than EG III and/or over expressed for EG III. Ultrafiltration is not a necessary requirement; however, the protein concentration should be kept to about 10 to 50 g/L.

Next 4 kg of polyethylene glycol average molecular weight 8000 and 14 kg of ammonium sulfate were added to the cellulase filtrate. The mixture was mixed in an overhead mixer for 18 hours. After mixing, the phases were allowed to separate for 18 hours. The bottom layer was removed through the bottom outlet in such a way as to maintain the phase separation. The PEG phase was collected and centrifuged at 5,000 xg for 30 minutes to remove any insoluble material. EG III activity is stable in the polyethylene glycol solution.

Removal of the protein from the polyethylene glycol exploits the fact that the polyethylene glycol is soluble in ethanol and the protein is not. This step also removes some of the salt and concentrates the protein. 200 ml aliquots of the PEG phase and 800 ml of cold ($-20°$ C.) ethanol were mixed well in one liter centrifuge bottles and allowed to sit for approximately 18 hours at $-20°$ C. The mixture was centrifuged at 5000 xg for 30 minutes, the solution was decanted and the precipitate rinsed with deionized water.

The choice of buffer for dissolution of the precipitated protein depends on the chromatographic steps which follow or, if this is the final step, in producing an enriched EG III solution. Generally, the buffer solutions are either 50 mM acetate, pH 5, or 10 mM citrate phosphate, pH 4 in preparation for cation exchange chromatography.

Recovery for the PEG extraction can be determined based on RBB-CMC activity, and total volumes are as shown below. The method of determining RBB-CMC activity is described in Example 3.

TABLE 1

| SAMPLE | DIL. | OD 590 | OD/ ml | VOLUME ml | TOTAL OD | RECOVERY % |
|---|---|---|---|---|---|---|
| BROTH | 40 | .299 | 12.0 | 4000 | 47840 | 100 |
| PEG | 100 | .193 | 19.3 | 510 | 9843 | 21 |
| RAFFINATE | 40 | .234 | 9.36 | 3490 | 32666 | 68 |

Recovery of activity ranges from 15 to 30 percent into the PEG phase. This step represents the highest loss as a percentage of total endoglucanase activity if the starting material is EG I/II deleted cellulase. The loss due to each subsequent chromatographic step tends to be small by comparison, approximately 20% or less for each step.

Chromatography

The enriched EG III solution from Example I, part (b) was diafiltered using an omega series tangential flow 8,000 ultra filtration membrane (Filtron Technology Corp., Northborough, Mass.) against 10 mM, pH 5 citrate/phosphate buffer. The solution was loaded onto an equilibrated (pH 5, 10 mM citrate/phosphate) SP Trisacryl column and the flow-through collected and the pH adjusted to 4 with 0.5M citric acid. The flow-through was next loaded onto an equilibrated (pH 4, 10 mM citrate/phosphate) SP Trisacryl column. The EG III component was eluted with 250 mM sodium chloride.

Example 2

Purification of EG III Via Fractionation

The purification of EG III is conducted by fractionation from a complete fungal cellulase composition (CYTOLASE 123 cellulase, commercially available from Genencor International, South San Francisco, Calif.) which is produced by wild type *Trichoderma longibrachiatum*. Specifically, the fractionation is done using columns containing the following resins: Sephadex G-25 gel filtration resin from Sigma Chemical Company (St. Louis, Mo.), QA Trisacryl M anion exchange resin and SP Trisacryl M cation exchange resin from IBF Biotechnics (Savage, Md.). CYTOLASE 123 cellulase, 0.5 g, is desalted using a column of 3 liters of Sephadex G-25 gel filtration resin with 10 mM sodium phosphate buffer at pH 6.8. The desalted solution, is then loaded onto a column of 20 ml of QA Trisacryl M anion exchange resin equilibrated with 10 mM sodium phosphate buffer pH=6.8. The fraction bound on this column contained CBH I and EG I. The fraction not bound on this column contains CBH II, EG II and EG III. These fractions are desalted using a column of Sephadex G-25 gel filtration resin equilibrated with 10 mM sodium citrate, pH 4.5. This solution, 200 ml, is then loaded onto a column of 20 ml of SP Trisacryl M cation exchange resin. The EG III was eluted with 100 mL of an aqueous solution of 200 mM sodium chloride.

One particular method for further purifying EG III is by further fractionation of an EG III sample obtained in this Example 2. The fractionation was done on a FPLC system using a Mono-S-HR 5/5 column (available from Pharmacia LKB Biotechnology, Piscataway, N.J.). The FPLC system consists of a liquid chromatography controller, 2 pumps, a dual path monitor, a fraction collector and a chart recorder (all of which are available from Pharmacia LKB Biotechnology, Piscataway, N.J.). The fractionation was conducted by desalting 5 ml of the EG III sample prepared in this Example 2 with a 20 ml Sephadex G-25 column which had been previously equilibrated with 10 mM sodium citrate pH 4. The solution was loaded onto mono-S-HR 5/5 column previously equilibrated with 10 mM sodium citrate pH=4.0 and then eluted with 0–200 mM aqueous gradient of NaCl at a rate of 0.5 ml/minute with samples collected in 1 ml fractions. EG III was recovered in fractions 10 and 11 and was determined to be greater than 90% pure by gel electrophoresis. EG III of this purity is suitable for determining the N-terminal amino acid sequence by known techniques.

Substantially pure EG III has the following characteristics which are compared to the other endoglucanases isolated from *Trichoderma longibrachiatum*.

TABLE 2

|        | MW        | pI  | pH optimum[1] |
|--------|-----------|-----|---------------|
| EG I   | ~47–49 kD | 4.7 | ~5            |
| EG II  | ~35 kD    | 5.5 | ~5            |
| EG III | ~25–28 kD | 7.4 | ~5.5–6.0      |

[1]pH optimum determined by RBB-CMC activity as per Example 3 below.

As can be seen from the above table, EG III has both a higher pH optimum and a higher pI as compared to the other endoglucanase components of *Trichoderma longibrachiatum*. In Example 3 below, it is seen that EG III also retains significant RBB-CMC activity under alkaline pHs.

Likewise, EG III cellulase from other sources including other strains of can be purified by the above methods. For example, EG III cellulase derived from *Trichoderma viride* has been described by Voragen et al., Methods in Enzymology, 160:243–249. This reference describes the EG III cellulase as having a molecular weight of about 23.5 Kdaltons, a pH optimum of 5.5, and a pI of 7.7.

In order to enhance the efficiency of the isolation of EG III, it may be desirable to employ *Trichoderma longibrachiatum* genetically modified so as to overexpress EG III and/or to be incapable of producing one or more of EG I, EG II, CBH I and/or CBH II components.

Likewise, it may be desirable for the EG III compositions described above to be further purified. For example, EG III protein isolated in Example 1 can be further purified by the above procedures or vice versa.

Example 3

Activity of Cellulase Compositions Over a pH Range

The following procedure was employed to determine the pH profiles of two different cellulase compositions. The first cellulase composition was a CBH I and II deleted cellulase composition prepared from *Trichoderma longibrachiatum* genetically modified in a manner similar to that described below so as to be unable to produce CBH I and CBH II components. Insofar as this cellulase composition does not contain CBH I and CBH II which generally comprise from about 58 to 70 percent of a cellulase composition derived from *Trichoderma longibrachiatum*, this cellulase composition is necessarily enriched in EG components. Since EG III is the most minor of the endoglucanase components of *Trichoderma longibrachiatum*, this composition predominates in EG I and EG II components.

The second cellulase composition was an approximately 20–40% pure fraction of EG III isolated from a cellulase composition derived from *Trichoderma longibrachiatum* via purification methods similar to Example 2.

The activity of these cellulase compositions was determined at 40° C. and the determinations were made using the following procedures.

Add 5 to 20 μl of an appropriate enzyme solution at a concentration sufficient to provide the requisite amount of enzyme in the final solution. Add 250 μl of 2 weight percent RBB-CMC (Remazol Brilliant Blue R-Carboxymethyl-cellulose —commercially available from MegaZyme, 6 Altona Place, North Rocks, N.S.W. 2151, Australia) in 0.05M citrate/phosphate buffer at pH 4, 5, 5.5, 6, 6.5, 7, 7.5 and 8.

Vortex and incubate at 40° C. for 30 minutes. Chill in an ice bath for 5 to 10 minutes. Add 1000 μl of methyl cellosolve containing 0.3M sodium acetate and 0.02M zinc acetate. Vortex and let sit for 5–10 minutes. Centrifuge and pour supernatant into cuvets.

Relative enzyme activity was determined by measuring the optical density (OD) of the solution in each cuvet at 590 nm. Higher levels of optical density correspond to higher levels of enzyme activity.

The results of this analysis are set forth in FIG. 1 which illustrates the relative activity of the CBH I and II deleted cellulase composition compared to the EG III cellulase composition. From this figure, it is seen that the cellulase composition deleted in CBH I and CBH II possesses optimum cellulolytic activity against RBB-CMC at near pH 5.5 and has some activity at alkaline pHs, i.e., at pHs from above 7 to 8. On the other hand, the cellulase composition enriched in EG III possesses optimum cellulolytic activity at about pH 5.5–6 and possesses significant activity at alkaline pHs.

Example 4

Isoelectric Focusing Gels

The purpose of this example is to illustrate isoelectric focusing gels of different EG III cellulase compositions. Specifically, cellulase produced by a wild type *Trichoderma longibrachiatum*; cellulase derived from a strain of *Trichoderma longibrachiatum* transformed by the method of Examples 16 and 17 so as to be incapable of expressing EG I and EG II cellulase proteins; and substantially pure EG III cellulase by the method similar to that of Example 1 were analyzed on isoelectric focusing gels.

Samples of these cellulases were analyzed by isoelectric focusing using a Pharmacia IEF system (FBE-3000, Pharmacia Inc., Piscataway, N.J.) and pH 3-10 precast gels (Servalyt Precote, available from Serva, Carl-Berg, Germany) according to the manufacturer's instructions. The gels were stained with Ephortec TM stain (Serva Blue W, available from Serva Fine Biochemicals, Westbury, N.Y. 11590) to visualize the protein bands. The resulting gel is set forth in FIG. 2 wherein Lane 1 of FIG. 2 illustrates the isoelectric focusing gel of cellulase derived from a wild strain *Trichoderma longibrachiatum*; Lane 2 illustrates the isoelectric focusing gel of cellulase derived from a strain of *Trichoderma longiburachiatum* so as to be incapable of expressing EG I and II; and Lane 3 illustrates the isoelectric focusing gel of substantially pure EG III cellulase. In this figure, the margin adjacent to Lane 1 is marked to identify the bands corresponding to cellulase proteins so as to permit identification of the proteins.

From the above figure, it is seen that because of EG III's high pI, this protein is found in a region usually associated with other high pI components such as high pI xylanases, high pI β-glucosidases, etc. Moreover, this Figure demonstrates that EG III is not a degradation product of either EG I or EG II proteins because, in Lane 2 of this Figure, these proteins are not present while the EG III protein is.

Example 5

Peptide Sequencing of EGIII

The EG III component was precipitated by the addition of 0.9 ml of acetone to 0.1 ml of protein solution (at a concentration of 1 mg/ml) and incubation at $-20°$ C. for 10 minutes. The protein was collected by centrifugation and the pellet dried and resuspended in 0.01 ml of 8 M urea in 88% formic acid and 0.01 ml of cyanogen bromide (200 mgml) in 88% formic acid. The mixture was incubated at room temperature for four hours.

Individual peptides were purified on a HPLC (high pressure liquid chromatography) column. A Synchropak RP-4 column was equilibrated in deionized milliQ water with 0.05% TEA (triethylamine) and 0.05% TFA (trifluoroacetic acid). The sample was loaded onto the HPLC column and elution was carried out with 100% acetonitrile and 0.05% TEA and 0.05% TFA, with a gradient of 1% per minute. The amino-terminal regions of isolated peptides were sequenced by the method of Edman using a fully automated apparatus. The amino acid sequence obtained from two fragments of the EG III component are shown in FIG. 3 (SEQ ID NOS: 1 and 2).

Example 6

Selection for pyr4 derivatives of *Trichoderma longibrachiatum*

The Pyr4 gene encodes orotidine-5'-monophosphate decarboxylase, an enzyme required for the biosynthesis of uridine. The toxic inhibitor 5-fluOroorotic acid (FOA) is incorporated into uridine by wild-type cells and thus poisons the cells. However, cells defective in the pyr4 gene are resistant to this inhibitor but require uridine for growth. It is, therefore, possible to select for pyr4 derivative strains using FOA. In practice, spores of *T. longibrachiatum* RL-P37 (Sheir-Neiss, G. and Montenecourt, B. S., *Appl. Microbiol. Biotechnol.* 20, p. 46-53 (1984)) were spread on the surface of a solidified medium containing 2 mg/ml uridine and 1.2 mg/ml FOA. Spontaneous FOA-resistant colonies appeared within three to four days and it was possible to subsequently identify those FOA-resistant derivatives which required uridine for growth. In order to identify those derivatives which specifically had a defective pyr4 gene, protoplasts were generated and transformed with a plasmid containing a wild-type pyr4 gene (see Examples 8 and 9). Following transformation, protoplasts were plated on medium lacking uridine. Subsequent growth of transformed colonies demonstrated complementation of a defective pyr4 gene by the plasmid-borne pyr4 gene. In this way, strain GC69 was identified as a pyr4 derivative of strain RL-P37.

Example 7

Preparation of CBHI Deletion Vector

A cbh1 gene encoding the CBHI protein was cloned from the genomic DNA of *T. ressei* strain RL-P37 by hybridization with an oligonucleotide probe designed on the basis of the published sequence for this gene using known probe synthesis methods (Shoemaker et al., 1983b). The cbh1 gene resides on a 6.5 kb PstI fragment and was inserted into PStI cut pUC4K (purchased from Pharmacia Inc., Piscataway, N.J.) replacing the Kan$^r$ gene of this vector using techniques known in the art, which techniques are set forth in Maniatis et al. (1989) and incorporated herein by reference. The resulting plasmid, pUC4K::cbh1 was then cut with HindIII and the larger fragment of about 6 kb was isolated and religated to give pUC4K::cbh1ΔH/H (see FIG. 4). This procedure removes the entire cbh1 coding sequence and approximately 1.2 kb upstream and 1.5 kb downstream of flanking sequences. Approximately, 1 kb of flanking DNA from either end of the original PstI fragment remains.

The *T. longibrachiatum* pyr4 gene was cloned as a 6.5 kb HindIII fragment of genomic DNA in pUC18 to form pTpyr2 (Smith et al., 1991) following the methods of Maniatis et al., supra. The plasmid pUC4K::cbhIΔH/H was cut with HindIII and the ends were dephosphorylated with calf intestinal alkaline phosphatase. This end dephosphorylated DNA was ligated with the 6.5 kb HindIII fragment containing the *T. longibrachiatum* pyr4 gene to give pΔCBHIpyr4. FIG. 4 illustrates the construction of this plasmid.

Example 8

Isolation of Protoplasts

Mycelium was obtained by inoculating 100 ml of YEG (0.5% yeast extract, 2% glucose) in a 500 ml flask with about $5 \times 10^7$ *T. longibrachiatum* GC69 spores (the pyr4 derivative strain). The flask was then incubated at $37°$ C. with shaking for about 16 hours. The mycelium was harvested by centrifugation at $2,750 \times g$. The harvested mycelium was further washed in a 1.2 M sorbitol solution and resuspended in 40 ml of a solution containing 5 mg/ml Novozym ® 234 solution (which is the trade name for a multicomponent enzyme system containing 1,3-alpha-glucanase, 1,3-beta-glucanase, laminarinase, xylanase, chitinase and protease from Novo Biolabs, Danbury, Conn.); 5 mg/ml MgSO$_4$.7-

H₂O; 0.5 mg/ml bovine serum albumin; 1.2 M sorbitol. The protoplasts were removed from the cellular debris by filtration through Miracloth (Calbiochem Corp, La Jolla, Calif.) and collected by centrifugation at 2,000×30 g. The protoplasts were washed three times in 1.2 M sorbitol and once in 1.2 M sorbitol, 50 mM CaCl₂, centrifuged and resuspended at a density of approximately 2×10⁸ protoplasts per ml of 1.2 M sorbitol, 50 mM CaCl₂.

Example 9

Transformation of Fungal Protoplasts with pΔCBHIpyr4

200 μl of the protoplast suspension prepared in Example 8 was added to 20 μl of EcoRI digested pACB-HIpyr4 (prepared in Example 7) in TE buffer (10 mM Tris, pH 7.4; 1 mM EDTA) and 50 μl of a polyethylene glycol (PEG) solution containing 25% PEG 4000, 0.6 M KCl and 50 mM CaCl₂. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1.2 M sorbitol and 50 mM CaCl₂ was added thereto and this solution was further mixed. The protoplast solution was then immediately added to molten aliquots of Vogel's Medium N (3 grams sodium citrate, 5 grams KH₂PO₄, 2 grams NH₄NO₃, 0.2 grams MgSO₄.7H₂O, 0.1 gram CaCl₂.2H₂O, 5 μg α-biotin, 5 mg citric acid, 5 mg ZnSO₄.7H₂O, 1 mg Fe(NH₄)₂.6H₂O, 0.25 mg CuSO.5H₂O, 50 μg MnSO₄.4H₂O per liter) containing an additional 1% glucose, 1.2 M sorbitol and 1% agarose. The protoplast/medium mixture was then poured onto a solid medium containing the same Vogel's medium as stated above. No uridine was present in the medium and therefore only transformed colonies were able to grow as a result of complementation of the pyr4 mutation of strain GC69 by the wild type pyr4 gene insert in pΔCBHIpyr4. These colonies were subsequently transferred and purified on a solid Vogel's medium N containing as an additive, 1% glucose and stable transformants were chosen for further analysis.

At this stage stable transformants were distinguished from unstable transformants by their faster growth rate and formation of circular colonies with a smooth, rather than ragged outline on solid culture medium lacking uridine. In some cases a further test of stability was made by growing the transformants on solid non-selective medium (i.e. containing uridine), harvesting spores from this medium and determining the percentage of these spores which will subsequently germinate and grow on selective medium lacking uridine.

Example 10

Analysis of the Transformants

DNA was isolated from the transformants obtained in Example 9 after they were grown in liquid Vogel's medium N containing 1% glucose. These transformant DNA samples were further cut with a PstI restriction enzyme and subjected to agarose gel electrophoresis. The gel was then blotted onto a Nytran membrane filter and hybridized with a ³²P-labelled pΔCBHIpyr4 probe. The probe was selected to identify the native cbh1 gene as a 6.5 kb PstI fragment, the native pyr4 gene and any DNA sequences derived from the transforming DNA fragment.

The radioactive bands from the hybridization were visualized by autoradiography. The autoradiograph is seen in FIG. 6. Five samples were run as described above, hence samples A, B, C, D, and E. Lane E is the untransformed strain GC69 and was used as a control in the present analysis. Lanes A-D represent transformants obtained by the methods described above. The numbers on the side of the autoradiograph represent the sizes of molecular weight markers. As can be seen from this autoradiograph, lane D does not contain the 6.5 kb CBHI band, indicating that this gene has been totally deleted in the transformant by integration of the DNA fragment at the cbh1 gene. The cbh1 deleted strain is called P37PΔCBHI. FIG. 5 outlines the deletion of the *T. longibrachiatum* cbh1 gene by integration through a double cross-over event of the larger EcORI fragment from pΔCBHIpyr5 at the cbh1 locus on one of the *T. longibrachiatum* chromosomes. The other transformants analyzed appear identical to the untransformed control strain.

Example 11

Analysis of the Transformants with pIntCBHI

The same procedure was used in this example as in Example 10, except that the probe used was changed to a ³²P-labelled pIntCBHI probe. This probe is a pUC-type plasmid containing a 2 kb BglII fragment from the cbh1 locus within the region that was deleted in pUC4K::cbh1ΔH/H. Two samples were run in this example including a control, sample A, which is the untransformed strain GC69 and the transformant P37PΔCBHI, sample B. As can be seen in FIG. 7, sample A contained the cbh1 gene, as indicated by the band at 6.5 kb; however the transformant, sample B, does not contain this 6.5 kb band and therefore does not contain the cbh1 gene and does not contain any sequences derived from the pUC plasmid.

Example 12

Protein Secretion by strain P37PΔCBHI

Spores from the produced P37PΔCBHI strain were inoculated into 50 ml of a Trichoderma basal medium containing 1% glucose, 0.14% (NH₄)2SO₄, 0.2% KH₂PO₄, 0.03% MgSO₄, 0.03% urea, 0.75% bactotryptone, 0.05% Tween 80, 0.000016% CuSO₄.5H₂O, 0.001% FeSO₄.7H₂O, 0.000128% ZnSO₄.7H₂O, 0.0000054% Na₂MoO₄.2H₂O, 0.0000007% MnCl.4H₂O). The medium was incubated with shaking in a 250 ml flask at 37° C. for about 48 hours. The resulting mycelium was collected by filtering through Miracloth (Calbiochem Corp.) and washed two or three times with 17 mMpotassium phosphate. The mycelium was finally suspended in 17 mM potassium phosphate with 1 mM sophorose and further incubated for 24 hours at 30° C. with shaking. The supernatant was then collected from these cultures and the mycelium was discarded. Samples of the culture supernatant were analyzed by isoelectric focusing using a Pharmacia Phastgel system and pH 3-9 precast gels according to the manufacturer's instructions. The gel was stained with silver stain to visualize the protein bands. The band corresponding to the cbh1 protein was absent from the sample derived from the strain P37PΔCBHI, as shown in FIG. 8. This isoelectric focusing gel shows various proteins in different supernatant cultures of *T. longibrachiatum*. Lane A is partially purified CBHI; Lane B is the supernatant from an untransformed *T. longibra-* chiatum culture; Lane C is the supernatant from strain P37PΔCBHI produced according to the methods of the present invention. The position of various cellulase components are labelled CBHI, CBHII, EGI, EGII, and EGIII. Since CBHI constitutes 50% of the total extracellular protein, it is the major secreted protein and hence is the darkest band on the gel. This isoelectric focusing gel clearly shows depletion of the CBHI protein in the P37PΔCBHI strain.

Example 13

Preparation of pPΔCBHII

The cbh2 gene of *T. longibrachiatum*, encoding the CBHII protein, has been cloned as a 4.1 kb EcoRI fragment of genomic DNA which is shown diagrammatically in FIG. 9A (Chen et al., 1987, *Biotechnology*, 5:274–278). This 4.1 kb fragment was inserted between the EcoRI sites of pUC4XL. The latter plasmid is a pUC derivative (constructed by R. M. Berka, Genencor International Inc.) which contains a multiple cloning site with a symmetrical pattern of restriction endonuclease sites arranged in the order shown here: EcORI, BamHI, SacI, SmaI, HindIII, XhoI, BglII, ClaI, BglII, XhoI, HindIII, SmaI, SacI, BamHI, EcoRI. Using methods known in the art, a plasmid, pPΔCBHII (FIG. 9B), has been constructed in which a 1.7 kb central region of this gene between a HindIII site (at 74 bp 3′ of the CBHII translation initiation site) and a ClaI site (at 265 bp 3′ of the last codon of CBHII) has been removed and replaced by a 1.6 kb HindIII- ClaI DNA fragment containing the *T. reesei* pyr4 gene.

The *T. longibrachiatum* pyr4 gene was excised from pTpyr2 (see Example 7) on a 1.6 kb NheI-sphI fragment and inserted between the SphI and XbaI sites of pUC219 to create p219M (Smith et al., 1991, *Curr. Genet*, 19 p. 27–33). The pyr4 gene was then removed as a HindIII-ClaI fragment having seven bp of DNA at one end and six bp of DNA at the other end derived from the pUC219 multiple cloning site and inserted into the HindIII and ClaI sites of the cbh2 gene to form the plasmid pPΔCBHII (see FIG. 9B).

Digestion of this plasmid with EcoRI will liberate a fragment having 0.7 kb of flanking DNA from the cbh2 locus at one end, 1.7 kb of flanking DNA from the cbh2 locus at the other end and the *T. longbrachiatum* pyr4 gene in the middle.

Example 14

Generation of a pyr4 Derivative of P37PΔCBHI

Spores of the transformant (P37PΔCBHI) which was deleted for the cbh1 gene were spread onto medium containing FOA. A pyr4 derivative of this transformant was subsequently obtained using the methods of Example 6. This pyr4 strain was designated P37PΔCBHIPyr26.

Example 15

Deletion of the cbh2 Gene in a Strain Previously Deleted for cbh1

Protoplasts of strain P37PΔCBHIPyr26 were generated and transformed with EcoRI digested pPΔCBHII according to the methods outlined in Examples 8 and 9.

Purified stable transformants were cultured in shaker flasks as in Example 12 and the protein in the culture supernatants was examined by isoelectric focusing. One transformant (designated P37PΔΔCBH67) was identified which did not produce any CBHII protein. Lane D of FIG. 8 shows the supernatant from a transformant deleted for both the cbh1 and cbh2 genes produced according to the methods of the present invention.

DNA was extracted from strain P37PΔΔCBH67, digested with EcoRI and Asp718, and subjected to agarose gel electrophoresis. The DNA from this gel was blotted to a membrane filter and hybridized with $^{32}$P-labelled pPΔACBHII (FIG. 10). Lane A of FIG. 10 shows the hybridization pattern observed for DNA from an untransformed *T. reesei* strain. The 4.1 kb EcoRI fragment containing the wild-type cbh2 gene was observed. Lane B shows the hybridization pattern observed for strain P37PΔΔCBH67. The single 4.1 kb band has been eliminated and replaced by two bands of approximately 0.9 and 3.1 kb. This is the expected pattern if a single copy of the EcoRI fragment from pPΔCBHII had integrated precisely at the cbh2 locus.

The same DNA samples were also digested with EcoRI and Southern blot analysis was performed as above. In this Example, the probe was $^{32}$P-labelled pIntCBHII. This plasmid contains a portion of the cbh2 gene coding sequence from within that segment of the cbh2 gene which was deleted in plasmid pPΔCBHII. No hybridization was seen with DNA from strain P37PΔΔCBH67 showing that the cbh2 gene was deleted and that no sequences derived from the pUC plasmid were present in this strain.

Example 16

Construction of pΔEGIpyr-3 and Transformation of a pyr4 deficient strain of *T. longibrachiatum*

The *T. reesei* egl1gene, which encodes EGI has been cloned as a 4.2 kb HindIII fragment of genomic DNA from strain RL-P37 by hybridization with oligonucleotides synthesized according to the published sequence (Pentilia et al., 1986, *Gene*, 45: 253–263; van Arsdell et al., 1987, *Bio/Technology*, 5: 60–64).

This DNA fragment was inserted at the HindIII site of pUC100. An internal 1 kb EcoRV fragment which extended from a position close to the middle of the EGI coding sequence to a position beyond the 3′ end of the coding sequence was removed by enzyme digestion and was replaced by ligation with a 2.2 BamHI - HindIII fragment containing the cloned *A. niger pyrG* gene (Wilson et al., 1988, *Nucl. Acids Res.* 16 p. 2339) to give pΔAEGIpyrG-3 (FIG. 11). Transformation of a pyr4 deficient strain of *T. reesei* (strain GC69) by the method set forth in Examples 8 and 9, with pΔAEGIpyr-3, after it had been digested with HindIII to release the fragment containing the pyrG gene with flanking regions from the egl1 locus at either end, led to transformants in which the genomic egl1 gene was disrupted by a mechanism outlined in FIG. 12. DNA was extracted from transformants, digested with HindIII, subjected to agarose gel electrophoresis and blotted onto a membrane filter. The filter was hybridized with radiolabelled pΔAEGIpyr-3. In the untransformed strain of *T. longibrachiatum* the egl1 gene was present on a 4.2 kb HindIII fragment of DNA. However, following deletion of the egl1 gene by integration of the desired fragment from pΔAEGIpyr-3 this 4.2 kb HindIII fragment disappeared and was replaced by a HindIII fragment approximately 1.2 kb larger in size. This pattern was observed for one transformant, which was designated ΔEGI-3.

Example 17

Construction of PAΔEGII-1 and Deletion of the EG II Gene

The egl3 gene, encoding EG II (also referred to in the literature as EG III), was cloned from *T. longibrachiatum* strain RL-P37 as a 4 kb PstI genomic DNA fragment by hybridization with oligonucleotides synthesized according to the published sequence (Saloheimo et al., 1988, *Gene* 63:11–21). This DNA fragment was inserted into the PstI site of pUC18. This plasmid, pEGII, was subsequently digested with EcoRV to remove the entire EG II coding region on an approximately 2 kb segment extending from a position approximately 180 bp 5' of the EGII coding region to a position a few hundred base pairs beyond the end of the coding region. This segment was replaced with an SspI fragment of *Aspergillus nidulans* genomic DNA containing the amdS gene (Corrick et al., 1987, *Gene* 53:63–71) to create plasmid PAΔEGII-1 (See FIG. 13).

Wild-type strains of *T. longibrachiatum* are unable to grow on acetamide as a sole nitrogen source. Transformation with the amdS gene confers this ability and this is the basis for the selection system for transformants containing this gene.

Protoplasts of strain ΔEGI-3 were transformed, by the methods described in Examples 10 and 11, with pAΔEGII-1 which had been digested with HindIII and EcoRI and transformants able to grow on acetamide were selected. Subsequently, DNA was extracted from stable transformants, digested with PstI, subjected to agarose gel electrophoresis and blotted onto a membrane filter. The filter was hybridized with radiolabelled pAΔΔEGII-1. Homologous integration of the HindIII-EcoRI fragment from pAΔΔEGII-1, which contained egl3 flanking regions and amdS, at the genomic egl3 locus in a transformant lead to the 4 kb genomic PstI fragment containing the egl3 gene being replaced by smaller Pst1 fragments including two which would be approximately 1.0 and 2.8 kb in length. This pattern of hybridization was observed for one transformant which was designated strain ΔΔEG-1. This strain has deletions in both the EGI and EGII encoding genes and consequently is unable to produce either of these proteins.

The methods described in Examples 7–17 and in U.S. Ser. No. 07/770,049, filed Oct. 4, 1991, (incorporated herein by reference in its entirety) may be used to obtain *T. longibrachiatum* transformants which are unable to produce any or all of the following cellulase components; EG I, EG II, CBHI and CBHII, and the xylanase components. Additionally, the methods described may be used to obtain a *T. longibrachiatum* transformant which overexpresses the EG III cellulase component.

While the invention has been described in terms of various preferred embodiments, the skilled artisan will appreciate that various modifications, substitutions omissions and changes may be made without departing from the spirit and scope thereof. Accordingly, it is intended that the scope of the present invention be limited solely by the scope of the following claims, including equivalents thereof.

What is claimed is:

1. A method for isolating EG III cellulase component substantially free of other cellulase proteins from an aqueous mixture containing cellulase proteins which method comprises i- adding an inorganic salt and polyethylene glycol having a molecular weight of from about 5,000 to 10,000 to the aqueous mixture of cellulase proteins under conditions to create a two-phase system wherein substantially all of the cellulase proteins, other than EG III, are retained in an EG III-poor aqueous phase and the EG III cellulase component is retained in an EG III-rich polyethylene glycol phase, ii- separating the polyethylene glycol, EG III-rich phase from the aqueous, EG-III poor phase and collecting said EG III-rich polyethylene glycol phase that is substantially free of other cellulase proteins in said aqueous mixture and iii- separating the EG III from the polyethylene glycol EG III-rich phase and collecting the EG III component.

2. The method according to claim 1 wherein EG III is separated from the polyethylene glycol EG III-rich phase by precipitation.

3. A method of claim 2 wherein a low molecular weight alcohol is added to the polyethylene glycol EG III-rich phase to precipitate the EG III.

4. A method of claim 3 wherein the low molecular weight alochol is ethanol.

5. A method of claim 1, wherein said inorganic salt is added to the aqueous mixture before the addition of the polyethylene glycol.

6. A method of claim 5, wherein the added inorganic salt is selected from the group consisting of sodium sulfate, magnesium sulfate ammonium sulfate, sodium phosphate and potassium phosphate.

7. A method of claim 1 wherein the beginning aqueous mixture is a filtered whole-cell extract.

8. A method of claim 1 wherein the beginning aqueous mixture is a cell-free cellulase mixture.

9. A method for isolating enriched EG III cellulase in polyethylene glycol that is substantially free of other cellulase proteins from an aqueous mixture containing cellulase proteins which method comprises i- adding an inorganic salt and polyethylene glycol having a molecular weight of from about 5,000 to 10,000 to the aqueous mixture of cellulase proteins under conditions to create a two-phase system wherein substantially all of the cellulase proteins, other than EG III, are retained in an EG III-poor aqueous phase and the EG III cellulase component is retained in an EG III-rich polyethylene glycol phase, and ii- separating the polyethylene glycol, EG III-rich phase from the aqueous, EG-III poor phase and collecting said EG III-rich polyethylene glycol phase that is substantially free of other cellulase proteins in said aqueous mixture.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 23 amino acids
( B ) TYPE: amino acid
( D ) TOPOLOGY: linear ( x i ) SEQUENCE DESCRIPTION: SEQ ID NO:1:

```
Ile Trp Leu Gly Lys Tyr Gly Asp Gly Pro Ile Gly Ser Ser Gln Gly
1               5                   10                  15

Xaa Val Asn Val Gly Gly Gln
            20
```

( 2 ) INFORMATION FOR SEQ ID NO:2:

( i ) SEQUENCE CHARACTERISTICS:
( A ) LENGTH: 26 amino acids
( B ) TYPE: amino acid
( D ) TOPOLOGY: linear ( x i ) SEQUENCE DESCRIPTION: SEQ ID NO:2:

```
Pro Thr Thr Ala Ser Trp Ser Tyr Ser Gly Ser Asn Ile Arg Ala Asn
1               5                   10                  15

Val Ala Tyr Asp Leu Phe Thr Ala Ala Asn
            20                  25
```